(12) United States Patent
Dunbar et al.

(10) Patent No.: US 12,105,102 B2
(45) Date of Patent: Oct. 1, 2024

(54) METHODS FOR QUANTIFYING INSULIN-LIKE GROWTH FACTOR-1 AND INSULIN-LIKE GROWTH FACTOR-2

(71) Applicant: UNIVERSITY OF UTAH RESEARCH FOUNDATION, Salt Lake City, UT (US)

(72) Inventors: Carmen Dunbar, Salt Lake City, UT (US); Amol O. Bajaj, Salt Lake City, UT (US); Mark M. Kushnir, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 18/128,840

(22) Filed: Mar. 30, 2023

(65) Prior Publication Data
US 2023/0349931 A1 Nov. 2, 2023

Related U.S. Application Data

(60) Provisional application No. 63/325,401, filed on Mar. 30, 2022.

(51) Int. Cl.
*G01N 33/74* (2006.01)
*G01N 33/68* (2006.01)

(52) U.S. Cl.
CPC ......... *G01N 33/74* (2013.01); *G01N 33/6851* (2013.01); *G01N 2333/65* (2013.01)

(58) Field of Classification Search
CPC . G01N 33/74; G01N 33/6851; G01N 2333/65
See application file for complete search history.

(56) References Cited

U.S. PATENT DOCUMENTS 6,107,623 A 8/2000 Bateman et al.
6,124,137 A 9/2000 Hutchens et al.
(Continued)

OTHER PUBLICATIONS

Waters Corp. "A Guide to Effective Method Development in Bioanalysis." (2008). Accessed via Web May 26, 2023. <https://www.waters.com/webassets/cms/library/docs/720002710en.pdf>. (Year: 2008).*

(Continued)

*Primary Examiner* — Jill A Warden
*Assistant Examiner* — Michael Paul Shimek
(74) *Attorney, Agent, or Firm* — Michael Best & Friedrich LLP

(57) ABSTRACT

Disclosed herein are methods of determining a concentration of IGF-1 and/or IGF-2 with improved sensitivity using high performance liquid chromatography (HPLC) and mass spectrometry (MS). The methods can achieve improved sensitivity by using a supercharging reagent as part of a mobile phase of the HPLC, which can increase the amount of specific charge states of IGF-1 and/or IGF-2 ions detected by MS. An example method includes subjecting a sample to HPLC, wherein the HPLC comprises a mobile phase including a supercharging reagent and an organic acid; ionizing the sample to produce one or more ions detectable by mass spectrometry; determining amounts of IGF-1 ions in an $8^+$ charge state by mass spectrometry; and relating the amount of the determined IGF-1 ions in the $8^+$ charge state to the concentration of IGF-1 in the sample.

19 Claims, 11 Drawing Sheets

(56) References Cited

U.S. PATENT DOCUMENTS

| | | | |
|---|---|---|---|
| 6,204,500 | B1 | 3/2001 | Whitehouse et al. |
| 6,268,144 | B1 | 7/2001 | Koster |
| 8,293,489 | B2 | 10/2012 | Henkin |
| 8,728,753 | B2 | 5/2014 | Krizman et al. |
| 9,791,457 | B2 | 10/2017 | Kas |
| 10,571,455 | B2 | 2/2020 | Yang et al. |
| 10,648,989 | B2 | 5/2020 | Bystrom et al. |
| 10,830,746 | B2 | 11/2020 | Clarke |
| 11,454,637 | B2 | 9/2022 | Bystrom et al. |
| 2011/0111512 | A1* | 5/2011 | Bystrom ............... G01N 33/74 250/282 |
| 2019/0064126 | A1 | 2/2019 | Hsiao et al. |
| 2021/0041462 | A1 | 2/2021 | Bystrom et al. |

OTHER PUBLICATIONS

Brenton, A. Gareth, and A. Ruth Godfrey. "Accurate mass measurement: terminology and treatment of data." Journal of the American Society for Mass Spectrometry 21.11 (2010): 1821-1835. (Year: 2010).*

Nshanian, Michael, et al. "Enhancing sensitivity of liquid chromatography-mass spectrometry of peptides and proteins using supercharging agents." International journal of mass spectrometry 427 (2018): 157-164. (Year: 2018).*

Howard, James W. The development of mass spectrometry-based methodologies for the high throughput quantitation of peptides in biological matrices. Diss. Loughborough University, 2018. (Year: 2018).*

Bults, Peter, et al. "Intact protein bioanalysis by liquid chromatography-high-resolution mass spectrometry." J Chromatogr B Analyt Technol Biomed Life Sci 1110.1111 (2019): 155-167. (Year: 2019).*

Judák, Péter, et al. "Doping control analysis of small peptides: a decade of progress." Journal of Chromatography B 1173 (2021): 122551. (Year: 2021).*

Algeciras-Schimnich, A., et al. "Failure of current laboratory protocols to detect lot-to-lot reagent differences: findings and possible solutions." Clinical Chemistry 59.8 (2013): 1187-1194.

Bancos, I., et al. "Evaluation of variables influencing the measurement of insulin-like growth factor-1." Endocrine Practice 20.5 (2014): 421-426.

Bredehöft, M. et al. "Quantification of human insulin-like growth factor-1 and qualitative detection of its analogues in plasma using liquid chromatography/electrospray ionisation tandem mass spectrometry." Rapid Communications in Mass Spectrometry: An International Journal Devoted to the Rapid Dissemination of Up-to-the-Minute Research in Mass Spectrometry 22.4 (2008): 477-485.

Cox Hd, et al. Interlaboratory agreement of insulin-like growth factor 1 concentrations measured by mass spectrometry. Clin Chem 2014;60:541-8, including supplementary data.

Ito Y, et al. Stability of frozen serum levels of insulin-like growth factor-I, insulin-like growth factor-II, insulin-like growth factor binding protein-3, transforming growth factor beta, soluble Fas, and superoxide dismutase activity for the JACC study. J Epidemiol. 2005; 15 Suppl 1: S67-73.

Maus, A., et al. "Center of mass calculation in combination with MS/MS allows robust identification of single amino acid polymorphisms in clinical measurements of insulin-like growth factor-1." Journal of proteome research 19.1 (2019): 186-193.

Metzler G et al. Method for continuous monitoring of electrospray ion formation. J Am Sos Mass Spectrom (2017) 28:2117-23.

Motorykin, I., et al. "Isotopic peak index, relative retention time, and tandem MS for automated high throughput IGF-1 variants identification in a clinical laboratory." Analytical Chemistry 93.34 (2021): 11836-11842.

Valeja, S. G., et al. "New reagents for enhanced liquid chromatographic separation and charging of intact protein ions for electrospray ionization mass spectrometry." Analytical chemistry 82.17 (2010): 7515-7519.

Bystrom, C.E. et al. "Narrow mass extraction of time-of-flight data for quantitative analysis of proteins: determination of insulin-like growth factor-1." Analytical chemistry 83.23 (2011): 9005-9010.

Merchant, M. et al. "Recent advancements in surface-enhanced laser desorption/ionization-time of flight-mass spectrometry." Electrophoresis: An International Journal 21.6 (2000): 1164-1177.

Wright, G. L., et al. "ProteinChip® surface enhanced laser desorption/ionization (SELDI) mass spectrometry: A novel protein biochip technology for detection of prostate cancer biomarkers in complex protein mixtures." Prostate Cancer and Prostatic Diseases 2.5-6 (1999): 264-276.

Judák et al. "DMSO Assisted Electrospray Ionization for the Detection of Small Peptide Hormones in Urine by Dilute-and-Shoot-Liquid-Chromatography-High Resolution Mass Spectrometry.", J. Am. Soc. Mass Spectrom 28 (2017) 1657-1665.

Lange et al. "Fully automated dried blood spot sample preparation enables the detection of lower molecular mass peptide and non-peptide doping agents by means of LC-HRMS." Anal. Bioanal. Chem. (2020).

Iavarone et al. "Effects of solvent on the maximum charge state and charge state distribution of protein ions produced by electrospray ionization." J. Am. Soc. Mass Spectrom. 11 (2000) 976-985.

Judák et al. "Urinary matrix effects in electrospray ionization mass spectrometry in the presence of DMSO." J. Mass Spectrom. 53 (2018) 1018-1021.

* cited by examiner

METHODS FOR QUANTIFYING INSULIN-LIKE GROWTH FACTOR-1 AND INSULIN-LIKE GROWTH FACTOR-2

CROSS-REFERENCE TO RELATED APPLICATION(S)

This application claims the benefit of U.S. Provisional Patent Application No. 63/325,401, filed on Mar. 30, 2022, which is incorporated by reference herein in its entirety.

TECHNICAL FIELD

The present disclosure relates to methods of quantifying Insulin-Like Growth Factor-1 (IGF-1) and Insulin-Like Growth Factor-2 (IGF-2) via high-performance liquid chromatography and high-resolution mass spectrometry.

INTRODUCTION

Enhanced sensitivity of methods for the quantification of IGF-1 and IGF-2 would be beneficial in the diagnosis and treatment of numerous diseases.

SUMMARY

In one aspect, disclosed are methods of determining a concentration of IGF-1 in a sample, the method comprising subjecting the sample to high-performance liquid chromatography (HPLC), wherein the HPLC comprises a mobile phase including a supercharging reagent and an organic acid; ionizing the sample to produce one or more ions detectable by mass spectrometry; determining an amount of IGF-1 ions in an $8^+$ charge state by mass spectrometry; and relating the amount of the determined IGF-1 ions in the $8^+$ charge state to the concentration of IGF-1 in the sample.

In another aspect, disclosed are methods of determining a concentration of IGF-2 in a sample, the method comprising subjecting the sample to HPLC, wherein the HPLC comprises a mobile phase including a supercharging reagent and an organic acid; ionizing the sample to produce one or more ions detectable by mass spectrometry; determining an amount of IGF-2 ions in an $8^+$ charge state by mass spectrometry, and relating the amount of the determined IGF-2 ions in the $8^+$ charge state to the concentration of IGF-2 in the sample.

In another aspect, disclosed are methods of determining a concentration of IGF-1 in a sample, the method comprising subjecting the sample to HPLC, wherein the HPLC comprises a mobile phase including dimethyl sulfoxide (DMSO), tetrahydrothiophene-1,1-dioxide, m-nitrobenzyl alcohol, or a combination thereof and an organic acid; ionizing the sample to produce one or more ions detectable by mass spectrometry; determining an amount of IGF-1 ions in an $8^+$ charge state by mass spectrometry, and relating the amount of the determined IGF-1 ions in the $8^+$ charge state to the concentration of IGF-1 in the sample.

In another aspect, disclosed are methods of determining a concentration of IGF-1 in a sample, the method comprising subjecting the sample to HPLC, wherein the HPLC comprises a primarily aqueous-based mobile phase and a primarily organic-based mobile phase, and wherein the primarily aqueous-based mobile phase, the primarily organic-based mobile phase, or both include DMSO, and an organic acid; ionizing the sample to produce one or more ions detectable by mass spectrometry; determining an amount of IGF-1 ions in an $8^+$ charge state by mass spectrometry, and relating the amount of the determined IGF-1 ions in the $8^+$ charge state to the concentration of IGF-1 in the sample.

DETAILED DESCRIPTION

Figure 1:
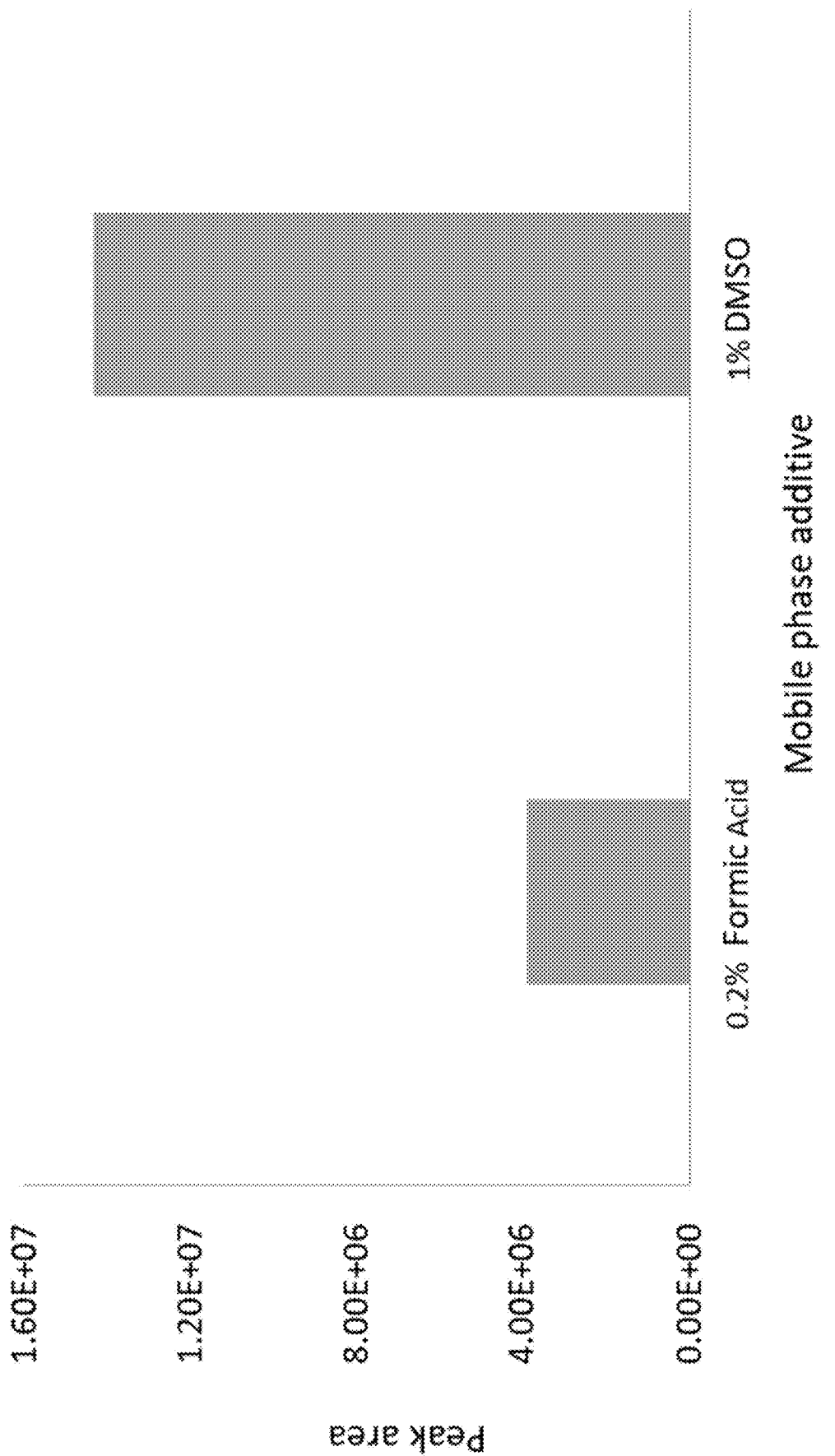
FIG. 1 shows a plot of peak area for IGF-1 (charge state $7^+$; m/z 1093.5216); chromatographic separation performed using mobile phase additives 0.2% formic acid and 1% DMSO. Charge states can be represented as, e.g., $7^+$ or $^+7$.

Methods are described herein that can measure IGF-1, IGF-2, or both using HPLC and mass spectrometry with improved sensitivity. The disclosed methods demonstrate by using a supercharging reagent, such as DMSO, in the mobile phase for HPLC, the relative abundance of ions with higher charge state (e.g., $8^+$ and $9^+$) for IGF-1 and/or IGF-2 is significantly increased when analyzed by mass spectrometry. This finding was surprising because other attempts of using a supercharging reagent to improve sensitivity of other polypeptides proved unsuccessful. Further, the increased abundance of the higher charge state ions of IGF-1 and/or IGF-2 enables enhanced sensitivity of analysis of IGF-1 and/or IGF-2 protein within a sample. For example, the disclosed methods can provide a lower limit of detection (LOD) for IGF-1 as low as 0.5 ng/ml—a marked improvement over LS-MS current methods.

1. DEFINITIONS

Unless otherwise defined, all technical and scientific terms used herein have the same meaning as commonly understood by one of ordinary skill in the art. In case of conflict, the present document, including definitions, will control. The materials, methods, and examples disclosed herein are illustrative only and not intended to be limiting. Methods and materials similar or equivalent to those described herein can be used in practice or testing of the disclosed invention. All publications, patent applications, patents and other references mentioned herein are incorporated by reference in their entirety.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are contemplated, and for the range 1.5-2, the numbers 1.5, 1.6, 1.7, 1.8, 1.9, and 2 are contemplated.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The term "high performance liquid chromatography" or "HPLC" (sometimes known as "high pressure liquid chromatography") refers to liquid chromatography in which the sample components interact with the mobile phase and stationary phase, and can be separated while traveling through the chromatographic column.

The term "IGF-1" refers to full-length IGF-1 polypeptides or fragments thereof, as well as full-length IGF-1 variant polypeptides or fragments thereof. IGF-1 variant polypeptides are readily recognized by one of skill in the art, including for example variants caused by single nucleotide polymorphisms and full-length IGF-1 polypeptides or fragments thereof that have been chemically modified. Example chemical modifications include, but are not limited to, reduction of one or more disulfide bridges or alkylation of one or more cystines. These example chemical modifications result in an increase in the mass of an IGF-1 variant polypeptide relative to the mass of the corresponding unmodified IGF-1 polypeptide. Reduction of one or more disulfide bridges results in a relatively minor change in the mass of the molecule, with the resulting mass to charge ratios falling within the mass to charge ratio ranges described herein. Other chemical modifications that result in a mass deviation from an unmodified IGF-1 polypeptide are also encompassed within the meaning of IGF-1. One skilled in the art understands that the addition of atoms to IGF-1 by chemical modification will result in an observed increase in the mass to charge ratios during mass spectrometry. Thus, IGF-1 variants that result from chemical modification are included within the meaning of IGF-1 and detectable in accordance with the disclosed methods.

The term "IGF-2" refers to full-length IGF-2 polypeptides or fragments thereof, as well as full-length IGF-2 variant polypeptides or fragments thereof. IGF-2 variant polypeptides are readily recognized by one of skill in the art, including for example full-length IGF-2 polypeptides or fragments thereof that have been chemically modified. Example chemical modifications may include reduction of one or more disulfide bridges or alkylation of one or more cystines. These example chemical modifications result in an increase in the mass of an IGF-2 variant polypeptide relative to the mass of the corresponding unmodified IGF-2 polypeptide. Reduction of one or more disulfide bridges results in a relatively minor change in the mass of the molecule, with the resulting m/z falling within the m/z ranges described herein. Other chemical modifications that result in a mass deviation from an unmodified IGF-2 polypeptide are also encompassed within the meaning of IGF-2. One skilled in the art understands that the addition of atoms to IGF-2 by chemical modification will result in an observed increase in the mass to charge ratios during mass spectrometry. Thus, IGF-2 variants that result from chemical modification are included within the meaning of IGF-2 and detectable in accordance with the methods of the invention.

The term "ionization" or "ionizing" refers to the process of generating an ion having a net electrical charge equal to one or more electron units. Negative ions are those having a net negative charge of one or more electron units, while positive ions are those having a net positive charge of one or more protons.

The term "liquid chromatography" refers to a separation technique in which the mobile phase is a liquid, where sample molecules are dissolved, with separation performed on a solid stationary phase. During the separation, the components of the mixture get distributed between the stationary phase and the fluid, (e.g., mobile phase), as this fluid moves relative to the stationary phase. Examples of separation techniques which employ "liquid chromatography" include reverse phase liquid chromatography (RPLC), high performance liquid chromatography (HPLC), and turbulent flow liquid chromatography (TFLC). In some embodiments, a solid-phase extraction (SPE) column may be used in combination with a liquid chromatography (LC) column.

The terms "lower limit of quantification", "lower limit of quantitation" or "LLOQ" refer to the point where measurements become quantitatively meaningful. The analyte response at this LLOQ is identifiable, discrete, and reproducible with a relative standard deviation (RSD %) of less than 20% and an accuracy of 80% to 120%.

The term "limit of detection" or "LOD" is the point at which the measured value is larger than the uncertainty associated with its measurement. The LOD is defined as the lowest concentration at which a compound can be qualitatively identified, while quantification may not be accurate.

The term "in-line" refers to a procedure performed without the need for operator intervention while the sample is analyzed on the instrument. In various embodiments of the methods, some steps may be performed in an on-line automated fashion.

The term "mass spectrometry" or "MS" refers to an analytical technique to identify compounds by their mass. MS refers to methods of separating, detecting, and measuring ions based on their mass-to-charge ratio, or "m/z". MS technology generally includes (1) ionizing the compounds to form charged compounds (i.e., ions); and (2) detecting such ions based on their mass-to-charge ratio. A "mass spectrometer" includes an ion source, mass analyzer, and an ion detector. During the analysis, molecules of interest are ionized, the ions are subsequently introduced into a mass spectrometer where, due to a combination of magnetic and electric fields, the ions follow a path in space that is dependent upon their mass to charge ratio ("m/z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., Prostate Cancer and Prostatic Diseases 1999, 2: 264-76; and Merchant and Weinberger, Electrophoresis 2000, 21: 1164-67, all of which are incorporated by reference herein in their entirety.

The term "sample" refers to any sample that may contain an analyte of interest.

The term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through a layer of solid phase, undesired components of the mobile phase may be retained by the solid phase resulting in a separation of the analyte of interest from the other sample constituents. In other instances, the analyte may be retained by the solid phase, allowing undesired components of the mobile phase to pass through the solid phase. In these instances, a mobile phase of a different composition is then used to elute the retained analyte from the solid phase for further processing or analysis. SPE may operate via a unitary or mixed mode mechanism. As used herein, SPE can be conducted with an extraction column or a cartridge.

2. METHODS

Disclosed herein are methods of determining an amount (e.g., concentration) of an insulin-like growth factor (IGF) in a sample. The insulin-like growth factors that can be determined by the disclosed methods include IGF-1 and IGF-2. In some embodiments, the method determines a concentration of IGF-1, IGF-2, or both in the sample. The sample in which the IGF-1 and/or IGF-2 is determined can be a biological sample. For example, the sample can be plasma or serum.

In some embodiments, the IGF is IGF-1. IGF-1 is a hormone with a molecular structure similar to insulin. IGF-1 is a polypeptide produced by the liver and contains 70 amino acids in a single chain with three intramolecular disulfide bridges. IGF-1 has a molecular weight of about 7,649 Da and is highly protein bound in serum. Production is stimulated by growth hormone and can be retarded by undernutrition, growth hormone insensitivity, lack of growth hormone receptors, or failure of a downstream signaling pathway. IGF-1 plays an important role in childhood growth and continues to have anabolic effects in adults.

In some embodiments, the IGF is IGF-2. IGF-2 is also a hormone with a molecular structure similar to insulin. It is a single chain peptide that contains 67 amino acids. IGF-2 has a molecular weight of about 7,505 Da and is also highly protein bound in serum. IGF-2 can be used as an adjunct to IGF-1 in clinical evaluation of growth hormone-related disorders. IGF-2 plays a role primarily in fetal growth and development by interacting with the IGF-1 receptor and other cell surface receptors and interacting with circulating binding proteins to modulate tissue growth. IGF-2 levels are reduced in children and adults as a result of growth hormone deficiency or malnutrition. Increased IGF-2 serum levels may be observed in acromegaly or with exogenous administration of IGF-1. Thus, measurement of circulating IGF-2 levels (e.g., in plasma/serum) is a useful tool in the management of several growth hormone-related disorders. In addition, measurement of circulating IGF-2 is also a valuable tool in various epidemiological research areas and clinical trials.

The IGF can be an intact protein. As used herein, the term "intact" in describing IGF refers to the full-length (e.g., unfragmented) polypeptide. Intact IGF-1, for example, is a polypeptide containing 70 amino acid residues.

A. High Performance Liquid Chromatography

The method includes subjecting the sample to HPLC. The HPLC can include a column through which the sample and mobile phase are passed. The column can include an inlet and an outlet; the sample may be injected directly in the inlet, or delivered from a SPE column, such as an on-line SPE cartridge.

The columns and cartridges can be packed with stationary phases, which can facilitate fractionation and separation of the sample constituents as the sample and the mobile phase pass through. The stationary phase can include particles, and/or porous monolithic materials. A surface of the stationary phase can include a bonded surface that can interact with various chemical moieties to facilitate separation of the molecules. One example bonded surface is a hydrophobic bonded surface such as an alkyl bonded or a cyano bonded surface. Alkyl bonded surfaces can include, but are not limited to, C-4 (e.g., 4 carbons), C-8, C-12, or C-18 bonded alkyl groups. In some embodiments, the column is a C-8 alkyl bonded column (e.g., Hypersil Gold C-8 column). In addition, the HPLC can use a variety of different columns depending on the type of separation needed. For example, the HPLC can include a reverse phase column, an ion-exchange column, or a size exclusion column. In some embodiments, the HPLC includes a reversed phase column.

The mobile phase can include a supercharging reagent. As used herein, the term "supercharging reagent" refers to a reagent (e.g., a solvent) that may aid in the ionization efficiencies of a protein in mass spectrometry analysis (e.g., electrospray ionization-MS). The supercharging reagent may improve the signal intensity and/or increase the generation of higher charge state ions for a molecule to be analyzed (i.e., an analyte). It has been found herein that supercharging reagents can be used to improve sensitivity of detection of IGF ions specifically in the $8^+$ charge state, which can advantageously lower the limit of detection (LOD) and the lower limit of quantification (LLOQ) for IGF proteins in a sample. Example supercharging reagents include, but are not limited to, dimethyl sulfoxide (DMSO), tetrahydrothiophene-1,1-dioxide, m-nitrobenzyl alcohol, and combinations thereof. In some embodiments, the supercharging reagent includes DMSO, tetrahydrothiophene-1,1-dioxide, or m-nitrobenzyl alcohol. In some embodiments, the supercharging reagent includes DMSO.

The supercharging reagent can be included in the mobile phase in varying amounts. For example, the mobile phase can include the supercharging reagent at about 0.5% to about 5% by volume of the mobile phase, such as about 0.6% to about 4%, about 0.7% to about 3%, about 0.8% to about 2%, about 0.5% to about 1.5%, about 0.5% to about 2%, or about 0.8% to about 1.2% by volume of the mobile phase. In some embodiments, the mobile phase includes the supercharging reagent at greater than 0.5%, greater than 0.6%, greater than 0.7%, greater than 0.8%, greater than 0.9%, greater than 1%, greater than 1.5%, or greater than 2% by volume of the mobile phase. In some embodiments, the mobile phase includes the supercharging reagent at less than 5%, less than 4.5%, less than 4%, less than 3.5%, less than 3%, less than 2.5, or less than 2% by volume of the mobile phase.

In some embodiments, the HPLC uses more than one type of mobile phase. For example, the HPLC can use two, three, four, five, or more different mobile phases. In some embodiments, the HPLC includes two mobile phases. In some embodiments, the HPLC includes two different mobile phases, a mobile phase that is primarily aqueous-based and a mobile phase that is primarily organic-based. In some embodiments, the primarily aqueous-based mobile phase includes the supercharging reagent, the primarily organic-based mobile phase includes the supercharging reagent, or both mobile phases include the supercharging reagent.

Other than the supercharging reagent, the mobile phase can include further components that can aid in the HPLC, the ionization, the MS, or some combination thereof. For example, the mobile phase can include an organic acid. Example organic acids include, but are not limited to, acetic acid, formic acid, difluoroacetic acid, and combinations thereof. In some embodiments, the organic acid includes acetic acid, formic acid, or difluoroacetic acid. In some embodiments, the organic acid includes acetic acid or formic acid. In some embodiments, the organic acid includes acetic acid. In some embodiments, the primarily aqueous-based mobile phase includes an organic acid and water. In some embodiments, the primarily organic-based mobile phase includes an organic acid and acetonitrile.

The mobile phase can include varying amounts of organic acid. For example, the mobile phase can include about 0.02% to about 0.3% organic acid by volume of the mobile phase, such as about 0.05% to about 0.3% organic acid, about 0.1% to about 0.3% organic acid, or about 0.15% to about 0.25% organic acid by volume of the mobile phase. In some embodiments, the mobile phase includes greater than or equal to 0.02% organic acid, greater than or equal to 0.05% organic acid, greater than or equal to 0.1% organic acid, greater than or equal to 0.125% organic acid, or greater than or equal to 0.15% organic acid by volume of the mobile phase. In some embodiments, the mobile phase includes less than or equal to 0.3% organic acid, less than or equal to 0.275% organic acid, less than or equal to 0.25% organic acid, less than or equal to 0.2% organic acid, or less than or equal to 0.15% by volume of the mobile phase.

In some embodiments, the primarily aqueous-based mobile phase includes, by percent volume of the primarily aqueous-based mobile phase, about 0.5% to about 5% supercharging reagent; and about 0.02% to about 0.3% organic acid, wherein the remaining balance is water. In some embodiments, the primarily aqueous-based mobile phase includes, by percent volume of the primarily aqueous-based mobile phase, about 0.5% to about 5% DMSO; and about 0.02% to about 0.3% acetic acid, wherein the remaining balance is water.

In some embodiments, the primarily organic-based mobile phase includes, by percent volume of the primarily organic-based mobile phase, about 0.5% to about 5% supercharging reagent; and about 0.02% to about 0.3% organic acid, wherein the remaining balance is acetonitrile. In some embodiments, the primarily organic-based mobile phase includes, by percent volume of the primarily organic-based mobile phase, about 0.5% to about 5% DMSO; and about 0.02% to about 0.3% acetic acid, wherein the remaining balance is acetonitrile.

Different mobile phase modes may be used for eluting the IGF. For example, HPLC may be performed using a gradient mode, an isocratic mode, or a polytyptic (i.e. mixed) mode. During chromatography, the separation of materials can be affected by variables such as mobile phase, elution mode, gradient conditions, temperature, and the like.

In preparation for HPLC and subsequent MS, an IGF may be enriched and/or purified relative to one or more other components in the sample (e.g. other proteins) by various methods known in the art, including, but not limited to, solid phase extraction (SPE), filtration, centrifugation, electrophoresis including capillary electrophoresis, affinity separations including immunoaffinity separations, and the use of chaotropic agents or any combination of the above or the like. In some embodiments, the method includes purifying the sample via on-line SPE prior to subjecting the sample to HPLC.

B. Mass Spectrometry

Following HPLC separation, the sample is analyzed via mass spectrometry. Mass spectrometry can be performed using a mass spectrometer, which can include an ion source for ionizing the sample constituents and producing one or more charged molecules (e.g., ions) that can be detectable by mass spectrometry. The sample can be ionized by any suitable method known within the art. For example, ionization of the sample may be performed by electron ionization, chemical ionization, electrospray ionization (ESI), atmospheric pressure chemical ionization (APCI), photoionization, atmospheric pressure photoionization (APPI), or matrix assisted laser desorption ionization (MALDI). The skilled artisan will understand that the choice of ionization method may be determined based on the analyte to be measured, type of sample, the type of detector, the choice of positive versus negative mode, etc. Depending on the particular ionization method and conditions employed, IGF-1 and/or IGF-2 may be ionized to a number of different charge states. The ionization source may be selected to minimize the dispersion of charge states generated to enrich for a specific set of charge states. In some embodiments, the ionizing is done by ESI. In some embodiments, rather than being in the mobile phase, the supercharging reagent can be supplied in the ion source as a separate stream. For example, there are ion source designs that can allow the delivery of solution inside the ion source using a two streams (with a separate pump).

While ionizing the sample can produce one or more ions detectable by mass spectrometry, it has been found that by using a supercharging reagent in the mobile phase, the method can more sensitively detect IGF by detecting the signal of IGF ions specifically in the $8^+$ charge state. Accordingly, the method can further include determining an amount (e.g., signal intensity or signal abundance) of IGF ions in an $8^+$ charge state by mass spectrometry. In some embodiments, an amount of IGF-1 ions, IGF-2 ions, or both in an $8^+$ charge state are determined by mass spectrometry. In some embodiments, an amount of IGF-1 ions in an $8^+$ charge state are determined by mass spectrometry.

In addition to the $8^+$ charge state, the $9^+$ charge state of IGF can be used in the disclosed methods. Accordingly, in some embodiments, the method can include determining an amount of IGF ions in a $9^+$ charge state by mass spectrometry. In some embodiments, an amount of IGF-1 ions, IGF-2 ions, or both in a $9^+$ charge state are determined by mass spectrometry. In some embodiments, an amount of IGF-1 ions in a $9^+$ charge state are determined by mass spectrometry. In some embodiments, the method includes determining an amount of IGF ions in both the $8^+$ charge state and the $9^+$ charge state by mass spectrometry.

Generally, after the sample has been ionized, the positively or negatively charged ions thereby created may be analyzed to determine a mass to charge ratio (m/z). Determining the amount of IGF ions in an $8^+$ charge state can be done by assessing the mass-to-charge (m/z) of the ion. For example, determining the amount of IGF-1 ions in an $8^+$ charge state can include determining the amount of an ion having a mass-to-charge ratio of 957.1±1 Da. Determining the amount of IGF-2 ions in an $8^+$ charge state can include determining the amount of an ion having a mass-to-charge ratio of 934.6±1 Da. Regarding IGF ions in the $9^+$ charge state, determining the amount of IGF-1 ions in a $9^+$ charge state can include determining the amount of an ion having a mass-to-charge ratio of 850.1±1 Da and/or determining the amount of IGF-2 ions in a $9^+$ charge state can include determining the amount of an ion having a mass-to-charge ratio of 830.6±1 Da.

A number of different analyzers can be used for the mass spectrometry analysis. Example analyzers for determining m/z include quadrupole analyzers, ion trap analyzers, time-of-flight analyzers, and orbitrap analyzers. In some embodiments, the mass spectrometry analyzer is a high resolution/high accuracy analyzer. For example, mass spectrometry can be conducted with a high resolution mass spectrometry instrument having a mass resolution of ≥10,000, ≥15,000, ≥20,000, ≥25,000, ≥30,000, or ≥35,000 and a mass accuracy of ≤50 ppm, ≤40 ppm, ≤30 ppm, ≤20 ppm, ≤15 ppm, ≤10 ppm, or ≤5 ppm. In some embodiments, the mass spectrometry is conducted with a high-resolution mass spectrometry instrument having a mass resolution of ≥30,000 and a mass accuracy of ≤15 ppm.

The method can further include relating the amount of the determined IGF ions in the $8^+$ and/or $9^+$ charge state to the concentration of IGF in the sample. The results of a sample analysis, e.g., a mass spectrum, may be related to the amount of the IGF in the original sample by numerous methods known in the art. For example, internal or external standards may be run with the samples, and a calibration curve constructed based on ions generated from those standards. Using such a calibration curve, the relative abundance of a given ion may be converted into an absolute amount of the original molecule. Accordingly, in some embodiments, the method includes adding an internal standard to the sample and determining an amount of IGF-1 and/or IGF-2. In some embodiments, the internal standard includes a stable isotope of IGF-1 and/or IGF-2. In some embodiments, the internal standard is $^{15}$N-labeled IGF-1 and/or 15N-labeled IGF-2. The internal standard can also be of the same charge state of that being analyzed.

By enhancing the signal of IGF ions in the $8^+$ charge state, the method can achieve an advantageous lower LOD of IGF. For example, the method can have a LOD for IGF-1 of less than or equal to 4.5 ng/mL, less than or equal to 4 ng/ml, less than or equal to 3.5 ng/ml, less than or equal to 3 ng/ml, less than or equal to 2.5 ng/ml, less than or equal to 2 ng/ml, less than or equal to 1.5 ng/mL, less than or equal to 1 ng/ml, less than or equal to 0.75 ng/mL, less than or equal to 0.5 ng/ml, less than or equal to 0.25 ng/ml, or less than or equal to 0.1 ng/ml. In some embodiments, the method has a LOD for IGF-1 of greater than or equal to 0.1 ng/ml, greater than or equal to 0.25 ng/ml, greater than or equal to 0.5 ng/ml, greater than or equal to 0.75 ng/ml, or greater than or equal to 1 ng/ml. In some embodiments, the method has a LOD for IGF-1 of about 0.1 ng/ml to about 4.5 ng/mL, such as about 0.1 ng/mL to about 4 ng/mL, about 0.25 ng/ml to about 4 ng/mL, about 0.25 ng/ml to about 3 ng/ml, about 0.25 ng/ml to about 2 ng/ml, about 0.25 ng/ml to about 1.5 ng/ml, or about 0.5 ng/ml to about 1 ng/ml. In some embodiments, the method has a LOD for IGF-1 of about 0.5 ng/ml.

The method can also have a LOD for IGF-2 of less than or equal to 7.5 ng/ml, less than or equal to 7 ng/ml, less than or equal to 6.5 ng/ml, less than or equal to 6 ng/mL, less than or equal to 5.5 ng/ml, less than or equal to 5 ng/ml, less than or equal to 4.5 ng/ml, less than or equal to 4 ng/ml, less than or equal to 3.5 ng/ml, less than or equal to 3 ng/ml, less than or equal to 2.5 ng/mL, less than or equal to 2 ng/ml, or less than or equal to 1.5 ng/ml. In some embodiments, the method has a LOD for IGF-2 of greater than or equal to 1.5 ng/ml, greater than or equal to 2 ng/ml, greater than or equal to 2.5 ng/mL, or greater than or equal to 3 ng/ml. In some embodiments, the method has a LOD for IGF-2 of about 1 ng/ml to about 8 ng/mL, such as about 1 ng/ml to about 7 ng/ml, about 1.5 ng/ml to about 5 ng/ml, or about 1 ng/ml to about 4 ng/ml. In some embodiments, the method has a LOD for IGF-2 of about 2 ng/mL.

The method may also achieve an advantageous lower LLOQ for IGF. For example, the method can have a LLOQ for IGF-1 of less than or equal to 14 ng/ml, less than or equal to 13 ng/mL, less than or equal to 12 ng/ml, less than or equal to 11 ng/ml, less than or equal to 10 ng/ml, less than or equal to 9 ng/ml, less than or equal to 8 ng/ml, less than or equal to 7 ng/mL, less than or equal to 6 ng/ml, less than or equal to 5 ng/mL, less than or equal to 4 ng/ml, less than or equal to 3 ng/ml, less than or equal to 2 ng/mL, less than or equal to 1 ng/ml, or less than or equal to 0.5 ng/ml. In some embodiments, the method has a LLOQ for IGF-1 of greater than or equal to 0.25 ng/ml, greater than or equal to 0.5 ng/ml, greater than or equal to 0.75 ng/ml, greater than or equal to 1 ng/mL, or greater than or equal to 2 ng/ml. In some embodiments, the method has a LLOQ for IGF-1 of about 0.25 ng/ml to about 14 ng/ml, such as about 0.25 ng/ml to about 12 mg/mL, about 0.5 ng/ml to about 10 ng/ml, about 0.5 ng/mL to about 8 ng/ml, about 0.75 ng/ml to about 5 ng/ml, or about 0.75 ng/mL to about 3 ng/ml. In some embodiments, the method has a LLOQ for IGF-1 of about 1 ng/ml.

The method can also have a LLOQ for IGF-2 of less than or equal to 29 ng/ml, less than or equal to 25 ng/ml, less than or equal to 20 ng/ml, less than or equal to 15 ng/ml, less than or equal to 10 ng/ml, less than or equal to 9 ng/ml, less than or equal to 8 ng/ml, less than or equal to 7 ng/ml, less than or equal to 6 ng/mL, less than or equal to 5 ng/ml, less than or equal to 4.5 ng/ml, less than or equal to 4 ng/ml, or less than or equal to 3 ng/ml. In some embodiments, the method has a LLOQ for IGF-2 of greater than or equal to 3 ng/ml, greater than or equal to 3.5 ng/mL, greater than or equal to 4 ng/ml, greater than or equal to 4.5 ng/ml, greater than or equal to 5 ng/ml, greater than or equal to 5.5 ng/ml, or greater than or equal to 6 ng/mL. In some embodiments, the method has a LLOQ for IGF-2 of about 3 ng/mL to about 29 ng/ml, such as about 3 ng/ml to about 25 ng/ml, about 3 ng/ml to about 20 ng/ml, about 4 ng/ml to about 15 ng/mL, about 4 ng/ml to about 10 ng/ml, or about 4 ng/ml to about 8 ng/ml. In some embodiments, the method has a LLOQ for IGF-2 of about 5 ng/ml.

Since the method can advantageously increase the signal of IGF ions in the $8^+$ charge state, the method can also increase the abundance of the signal of IGF ions in the $8^+$ charge state relative to the abundance of the signal of IGF ions in the 6+ and 7+ charge state. For example, the method can increase abundance of a mass spectrometry signal of the IGF-1 ions in the 8+ charge state by greater than or equal to 2%, greater than or equal to 3%, greater than or equal to 4%, greater than or equal to 5%, greater than or equal to 6%, greater than or equal to 7%, greater than or equal to 8%, greater than or equal to 9%, or greater than or equal to 10% compared to a method that does not include DMSO in the mobile phase, wherein the percentage of the mass spectrometry signal of the IGF-1 ions in the 8+ charge state is based on a mass spectrometry signal of a total amount of IGF-1 ions in a charge state of 6+, 7+, 8+, and 9+ in the sample.

In some embodiments, the method can increase a percentage of a mass spectrometry signal of the IGF-1 ions in the 8+ charge state by less than or equal to 15%, less than or equal to 12%, less than or equal to 10%, less than or equal to 9%, less than or equal to 8%, or less than or equal to 7% compared to a method that does not include DMSO in the mobile phase, wherein the percentage of the mass spectrometry signal of the IGF-1 ions in the 8+ charge state is based on a mass spectrometry signal of a total amount of IGF-1 ions on a charge state of 6+, 7+, 8+, and 9+ in the sample.

In some embodiments, the method can increase a percentage of a mass spectrometry signal of the IGF-1 ions in the 8+ charge state by about 2% to about 15%, such as about 2% to about 12%, about 3% to about 10%, or about 3% to about 6% compared to a method that does not include DMSO in the mobile phase, wherein the percentage of the mass spectrometry signal of the IGF-1 ions in the 8+ charge state is based on a mass spectrometry signal of a total amount of IGF-1 ions on a charge state of 6+, 7+, 8+, and 9+ in the sample.

As discussed elsewhere, the method can increase the absolute signal intensity of IGF-1 ions in the 8+ charge state. In some embodiments, the method increases the absolute signal intensity of IGF-1 ions in the 8+ charge state from about 1.5-fold to about 10-fold compared to a method that does not include DMSO in the mobile phase, such as about 2-fold to about 6-fold, about 2.5-fold to about 4.5-fold, or about 3-fold to about 4-fold compared to a method that does not include DMSO in the mobile phase. In some embodiments, the method increases the absolute signal intensity of IGF-1 ions in the 8+ charge state by greater than or equal to 1.5-fold, greater than or equal to 2-fold, or greater than or equal to 3-fold compared to a method that does not include DMSO in the mobile phase. In some embodiments, the method increases the absolute signal intensity of IGF-1 ions in the 8+ charge state by less than or equal to 10-fold, less than or equal to 8-fold, or less than or equal to 5-fold compared to a method that does not include DMSO in the mobile phase.

The disclosed invention has multiple aspects, illustrated by the following non-limiting examples.

3. EXAMPLES

Example 1

Example Method

Equipment and Supplies: Mass Spectrometer Exploris 240, equipped with electrospray ion source, operated in positive ion mode, full scan acquisition operated using software TraceFinder 5.1 (Thermo Scientific). The system utilizes four HPLC pumps (Thermo Vanquish series) with a DWL CTC PAL autosampler.

LC separation method is as follows: 1st dimensions separation performed on guard cartridge CN 4×3 mm, (SecurityGuard, AJ0-4305, Phenomenex); HPLC column for analytical separation (2nd dimension separation) Hypersil Gold C8, 2.1×50, 5 μm (part #25205-052130, Thermo Fisher). The 1st and 2nd dimension columns are connected to a high pressure 6-port switching valve. Mobile phase for 1st dimension columns: Bottle A—water with 0.2% formic acid. Bottle B—Acetonitrile, with 0.2% formic acid Bottle C—80% Acetonitrile, 20% 2-Propanol with 0.2% formic acid—Mobile phase for 2nd dimension column: Bottle A—water with 1% DMSO and 5 mM acetic acid. Bottle B—acetonitrile with 1% DMSO and 5 mM acetic acid Autosampler aqueous wash solvent A: water with 0.1% formic acid; autosampler organic wash solvent B: 30% acetonitrile/30% methanol/30% isopropanol/10% water.

HPLC pump programs:

TABLE 1

Gradient program for 1st dimension (loading pumps).

| Step | Time (min) | Length (min) | Flow (mL/min) | A (%) | B (%) | C (%) |
|---|---|---|---|---|---|---|
| 0 | 0 | 0.5 | 1 | 95 | 5 | 0 |
| 1 | 0.5 | 0.5 | 0.2 | 95 | 5 | 0 |
| 2 | 1 | 1 | 1 | 70 | 30 | 0 |
| 3 | 2 | 0.1 | 1 | 70 | 30 | 0 |
| 4 | 2.1 | 1.5 | 1 | 70 | 30 | 0 |
| 5 | 3.6 | 1 | 1.5 | 10 | 0 | 90 |
| 6 | 4.6 | 1 | 1.5 | 90 | 0 | 10 |
| 7 | 5.6 | 1 | 1.5 | 10 | 0 | 90 |
| 8 | 6.6 | 1.2 | 1 | 95 | 5 | 0 |

TABLE 2

Gradient program for 2nd dimension (eluting pumps).

| Step | Time (min) | Length (min) | Flow (mL/min) | % A | % B |
|---|---|---|---|---|---|
| 0 | 0 | 0.5 | 0.6 | 95 | 5 |
| 1 | 0.5 | 0.5 | 0.4 | 95 | 5 |
| 2 | 1 | 1 | 0.6 | 95 | 5 |
| 3 | 2 | 0.1 | 0.6 | 75 | 25 |
| 4 | 2.1 | 1.5 | 0.6 | 55 | 45 |
| 5 | 3.6 | 1 | 0.6 | 50 | 50 |
| 6 | 4.6 | 1 | 0.6 | 90 | 10 |
| 7 | 5.6 | 1 | 0.6 | 50 | 50 |
| 8 | 6.6 | 1.2 | 0.6 | 95 | 5 |

TABLE 3

Mass Spectrometer conditions

| | |
|---|---|
| Application Mode | Peptide |
| Method Duration (min) | 3.6 |
| Infusion mode | Liquid Chromatography |
| Default Charge State | 8 |
| Internal Mass Calibration | RunStart EASY-IC ™ |
| Global Parameters | Ion Source Type: H-ESI |
| | Spray Voltage: Static |
| | Positive Ion (V): 2900 |
| | Negative Ion (V): 2000 |
| | Gas Mode: Static |
| | Sheath Gas: 30 |
| | Aux Gas: 10 |
| | Sweep Gas: 2 |
| | Ion Transfer Tube Temp (° C.) 325 |
| | Vaporizer Temp (° C.) 300 |

TABLE 3-continued

| Mass Spectrometer conditions | |
|---|---|
| Scan Parameters | Scan Range (m/z) 800-1300 |
| | Orbitrap Resolution 120000 |
| | RF Lens (%) 120 |
| | AGC Target: Standard |
| | Maximum Injection Time Mode: Auto |
| | Microscans: 1 |
| | Data Type: Profile |
| | Polarity: Positive |

Mass-to-charge ratios (m/z) used in the data analysis method are listed in Table 4.

TABLE 4

| Mass-to-charge ratios (m/z) used in the data analysis method | | |
|---|---|---|
| Quantitation m/z (Da) | Confirming m/z (Da) | Compound |
| 957.0811 | 957.2061 | IGF-1 |
| 968.6720 | 968.5464 | $^{15}$N-labeled IGF-1 |

Calibration: A 6-point calibration curve for IGF-1 is prepared with every batch of samples by spiking mass spec gold serum matrix (MSGS, MSG3000, Golden West Diagnostics) with IGF-1 standards. The targeted IGF-1 concentrations in the calibrators are 10, 50, 100, 300, 600, and 1200 ng/ml.

Quality Control: Negative control (MSGS), controls containing low, medium, high concentrations of IGF-1, are analyzed with every batch of samples.

Sample preparation: (1) Prepare and print layout of the 96-well tube rack with sample IDs (8 wells per column, up to 12 columns). (2) Defrost specimens, controls and calibrators and let equilibrate at room temperature (RT; 18-24° C.). (3) While samples thaw, label three 96 deep-well plates with the date and run number. (4) When the calibrators, controls and samples are defrosted, mix contents of the tubes by inverting racks with the tubes 15-20 times. (5) Centrifuge tubes with calibrators and controls at 1,000×g for 1 min. (6) Prepare calibrators and aliquot in wells of the 96-well plate (plate #1). (7) Aliquot 100 μL of samples and controls into the corresponding wells of 96 well plate (plate #1). (8) Add to each sample and control 20 μL of $^{15}$N-labeled IGF-1 internal standard. (9) Secure silicon plate mat on top of plate and set the plate on orbital mixer (mix at 500 rpm for 30 min). (10) Remove plate mat and add to each well 400 μL of acidified ethanol (87.5% Ethanol 12.5% HCl). (11) Secure silicon plate mat and mix on plate mixer at 500 rpm for 15 mins at RT. (12) Centrifuge plate at 4° C. at 2,000×g for 20 mins. (13) Remove plate mat, transfer 300 μL of the supernatant to a new 96 well plate (plate #2). (14) Add to the wells 60 μL of cold 1.5 M Tris. (15) Secure silicon plate mat and set the plate on orbital mixer (mix at 500 rpm for 5 min). (16) Incubate the 96 well plate (plate #2) at −20° C. for 30 mins. (17) Centrifuge plate at 4° C. at 3,200×g for 10 mins. (18) Add 150 μL CLRW to a new 96 well plate. (19) Remove plate mat from the wells of 96-well plate #2 and transfer 150 μL of the supernatant into the 96 well plate containing 150 μL CLRW (plate #3). (20) Seal plate with foil, set the plate on orbital mixer (mix at 500 rpm for 5 min). (21) Centrifuge plate at 4° C. at 3,200×g for 5 mins.

Example 2

DMSO as a Supercharging Reagent

Sample Preparation

Sample preparation was performed as follows, 100 μL of calibrators, controls and serum/plasma samples were aliquoted into the corresponding wells of a deep-well 96 well plate. 20 μL of $^{15}$N-labeled IGF-1 (ProSpec Bio) internal standard was added to each well, the plate was sealed with silicon plate mat and incubated on an orbital mixer (500 rpm) for 30 min. After the incubation, 400 μL of acidified ethanol (87.5% Ethanol 12.5% HCl) was added into the wells, the plate was sealed and incubated on the orbital mixer (500 rpm) for 15 min, then centrifuged (2,000 g) at 4° C. for 20 min. After the centrifugation, 300 μl of the supernatants were transferred into wells of a new 96-well plate, and 60 μL of cold (6±4° C.) 1.5 M Tris buffer was added into the wells. The plate was sealed and incubated on the orbital mixer (500 rpm) for 5 min, then set inside a −20° C. freezer for 30 min, followed by centrifugation (3,200 g) 4° C. for 15 min. After the centrifugation, 150 μL of the supernatants were transferred from the 96-well into the wells of a new 96-well plate, and 150 μL of distilled water was added into the wells. The plate was sealed with foil, set on the orbital mixer (500 rpm) for 5 mins, then centrifuged (3,200 g) at 4° C. for 10 mins. The final 96 well plate was set in the tray of the autosampler and the samples were analyzed.

Effect of DMSO Addition to the Mobile Phase

Figure 2:
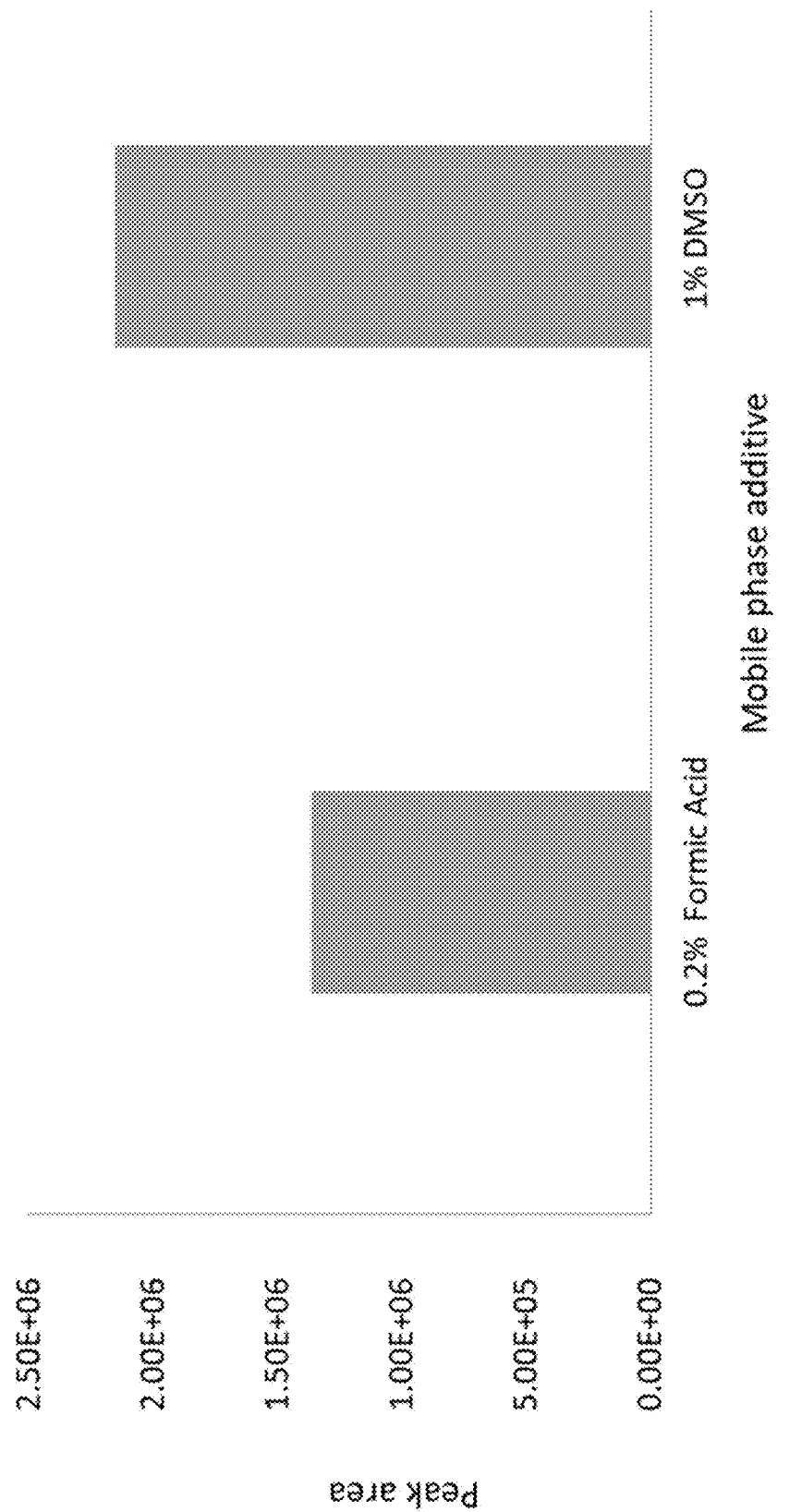
FIG. 2 shows a plot of peak area for IGF-2 (charge state $7^+$; m/z 1067.9361); chromatographic separation performed using mobile phase additives 0.2% formic acid and 1% DMSO.

Evaluation of sensitivity for IGF-1 and IGF-2 using mobile phase containing DMSO and without DMSO. Evaluation of the effect of percent of dimethyl sulfoxide (DMSO) addition to the mobile phase, on the method's sensitivity was performed by analysis of prepared serum samples containing IGF-1 using mobile phase A containing and not containing DMSO. Samples were prepared and analyzed using the same HPLC method and the same mobile phase B (0.2% formic acid in acetonitrile) but using composition of mobile phase A: i. 0.2% formic acid in water, ii. 1% DMSO in water. The observed enhancement in the signal intensity IGF-1 using mobile phase containing 1% DMSO as compared to 0.2% formic acid was 4-fold (FIG. 1), for IGF-1, and 1.7-fold for IGF-2 (FIG. 2).

Figure 3:
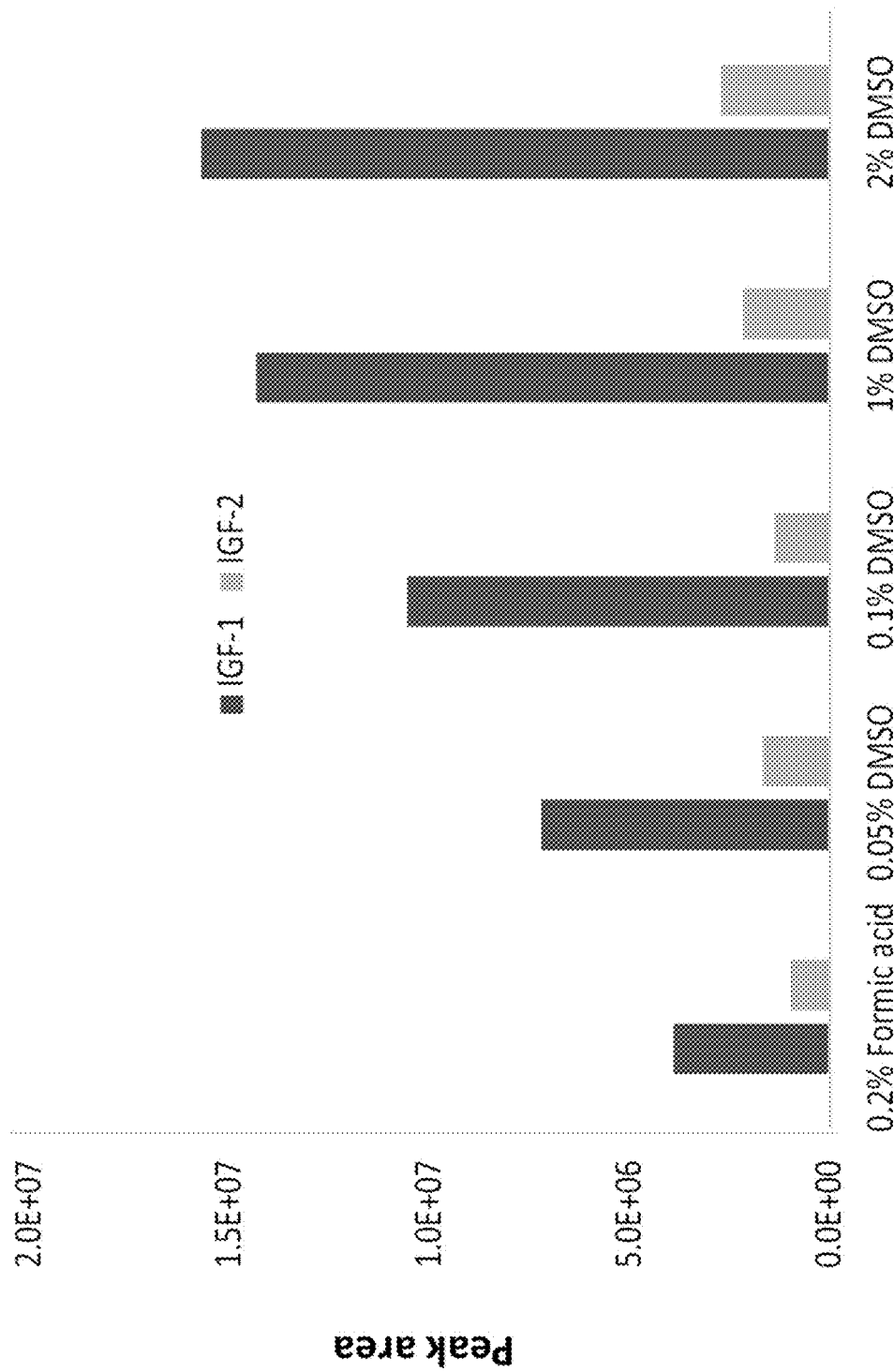
FIG. 3 shows IGF-1 and IGF-2 peak area in sample analyzed using mobile phases containing no DMSO and with addition of DMSO at concentrations ranging between 0.05 and 2%.

Evaluation of the effect of DMSO addition to the mobile phase, on the method's sensitivity was performed by analysis of prepared serum samples containing IGF-1 using mobile phase A with different composition (below) and mobile phase B containing 0.2% formic acid in acetonitrile. Evaluated additives to the aqueous mobile phases A were: i. 0.2% formic acid in water ii. 0.2% formic acid and 0.05%% DMSO, iii. 0.2% formic acid and 0.1% DMSO, iv. 0.2% formic acid and 1% DMSO, and v. 0.2% formic acid and 2% DMSO. The observed enhancement in the signal (FIG. 3) intensity in the mobile phase containing 2% DMSO in comparison with the use of mobile not containing DMSO for IGF-1 was 4-fold, and 2.8-fold for IGF-2.

Figure 4:
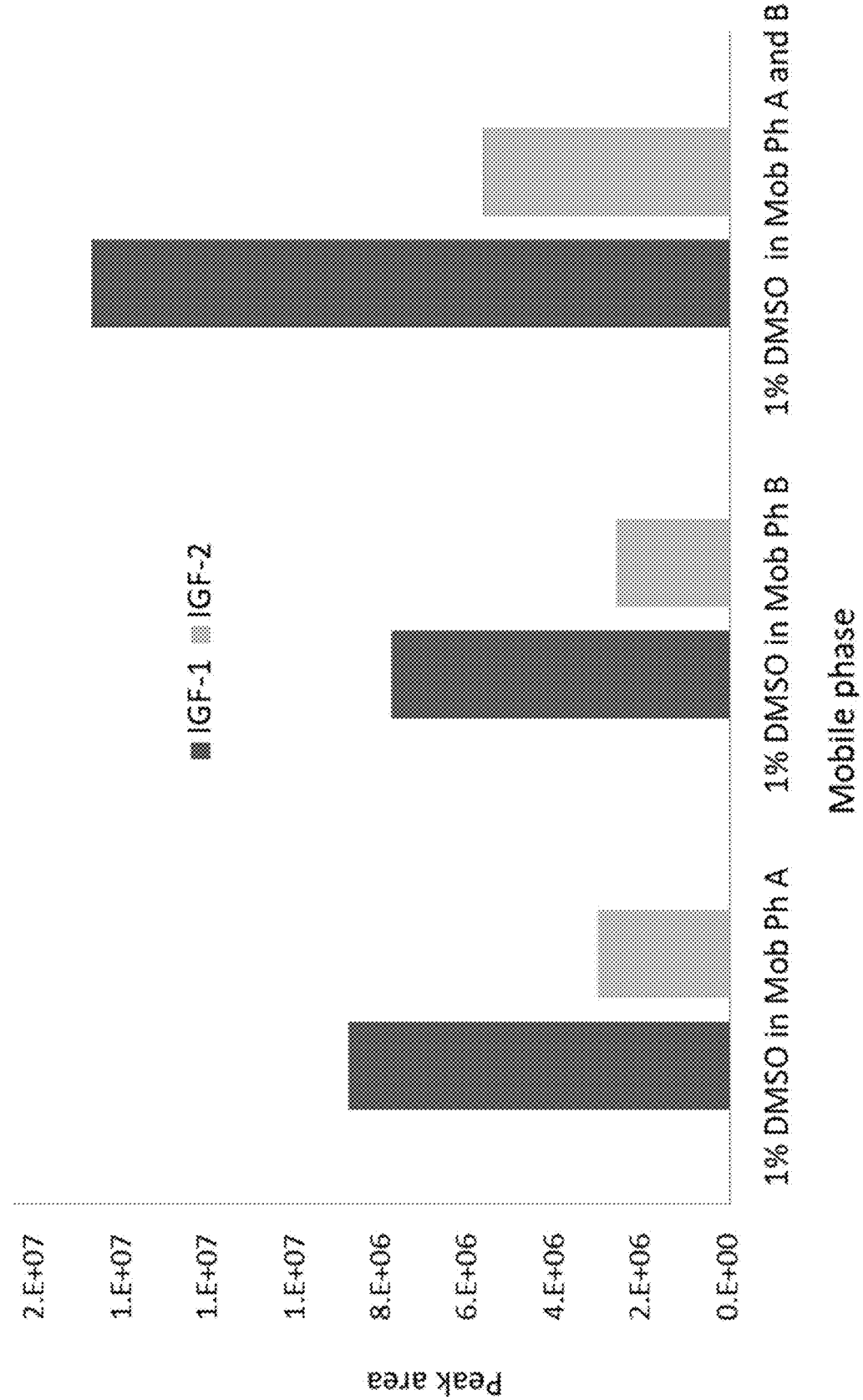
FIG. 4 shows a plot of peak area for IGF-1 (charge state $7^+$, m/z 1093.5216) and IGF-2 (charge state $7^+$, 1067.9361); chromatographic separation performed using 1% DMSO added only to mobile phase A, only to mobile phase B, and to both mobile phases.

Evaluation of the effect of DMSO addition to one of the mobile phases components vs both mobile phase components. Evaluation of the effect of DMSO addition to one of the mobile phases (A or B) or both mobile phases (A and B) was performed by analysis of prepared serum samples containing IGF-1 using mobile phases of different composition. Samples were prepared and analyzed by the same HPLC method while using i. mobile phase A: 0.2% formic acid, 1% DMSO in water, mobile phase B: 0.2% formic acid in acetonitrile; ii. mobile phase A: 0.2% formic acid in water, mobile phase B: 0.2% formic acid, 1% DMSO in acetonitrile; iii. mobile phases A: 0.2% formic acid, 1% DMSO in water, mobile phase B: 0.2% formic acid, 1% DMSO in acetonitrile. The observed signal enhancement (FIG. 4) using both mobile phase components containing 1% DMSO (A and B) resulted in 1.8-fold increase in the signal of IGF-1 and 2-fold increase in the signal of IGF-2.

Figure 5:
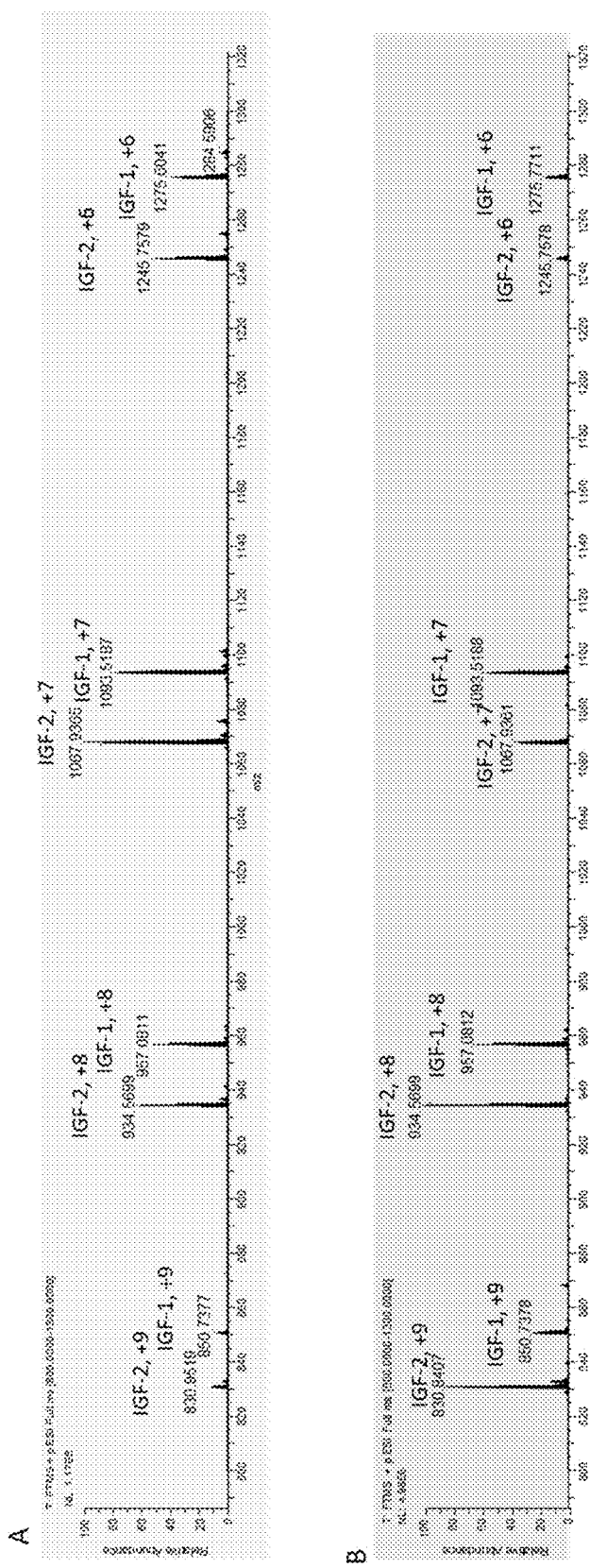
FIG. 5 shows a shift in the dominant charge state (from $6^+$ and $7^+$ to $8^+$ and $9^+$) in the presence of 1% DMSO for IGF-1 and IGF-2. Samples were analyzed with chromatographic separation performed using mobile phase containing 0.2% formic acid (A) and 1% DMSO (B) modifiers.

Comparison of signal intensity of charge state $7^+$ and $8^+$ IGF-1 and IGF-2 ions using mobile phase containing DMSO and mobile phase without DMSO. FIG. 5 shows IGF-1 and IGF-2 mass spectra acquired using mobile phases containing 0.2% formic acid (A), and mobile phase containing 0.2% formic acid and 1% DMSO (B). Using DMSO containing mobile phase, absolute signal intensity of the charge $8^+$ ions increased compared to the charge $7^+$ ions by 3.3-fold for IGF-1, and 6.1-fold for IGF-2.

Figure 6:
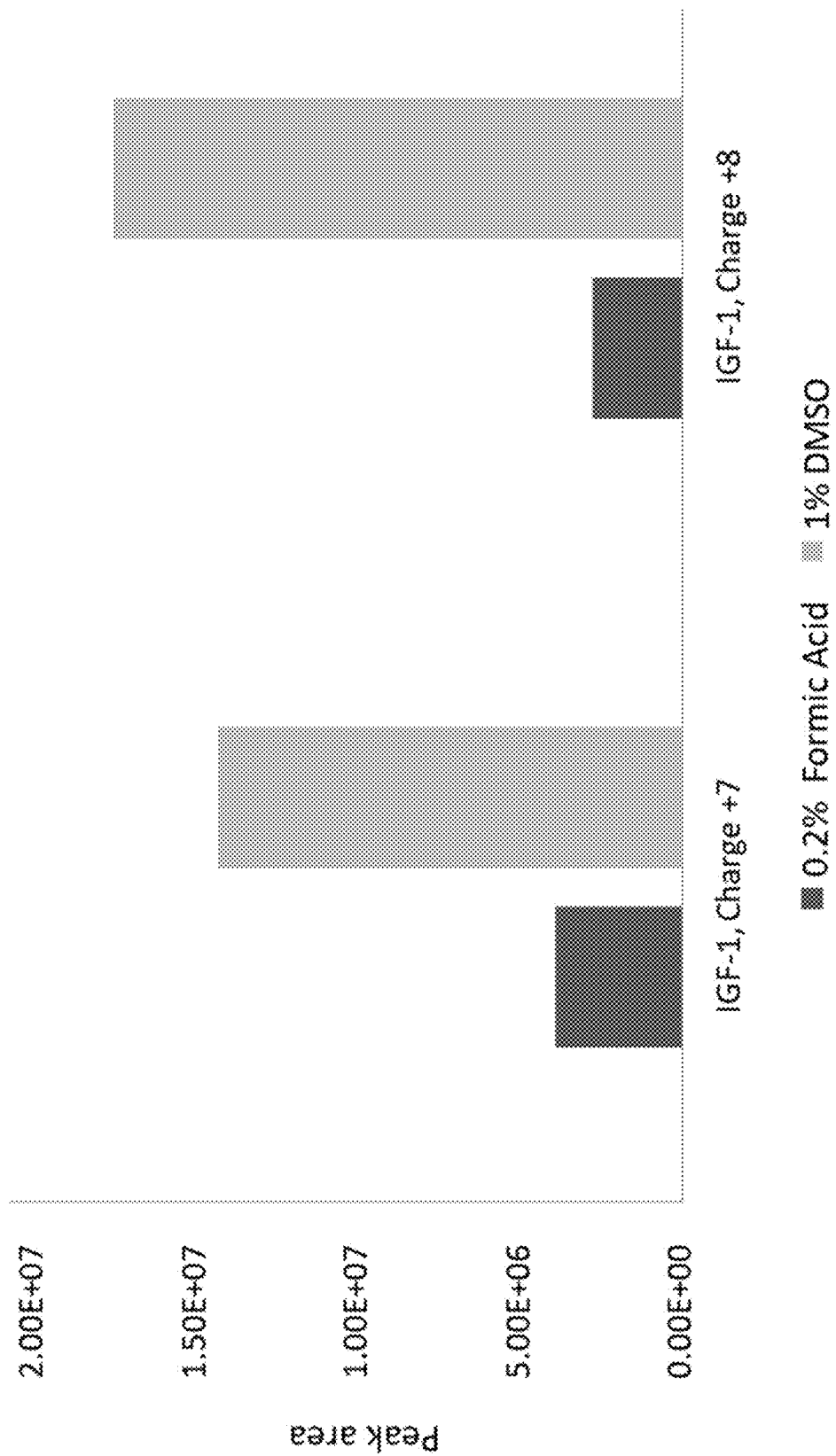
FIG. 6 shows a shift in the dominant charge state (from $7^+$ to $8^+$) in presence of DMSO for IGF-1. IGF-1 charge state $7^+$, m/z 1093.5216 and charge state $8^+$, m/z 957.0811.
Figure 7:
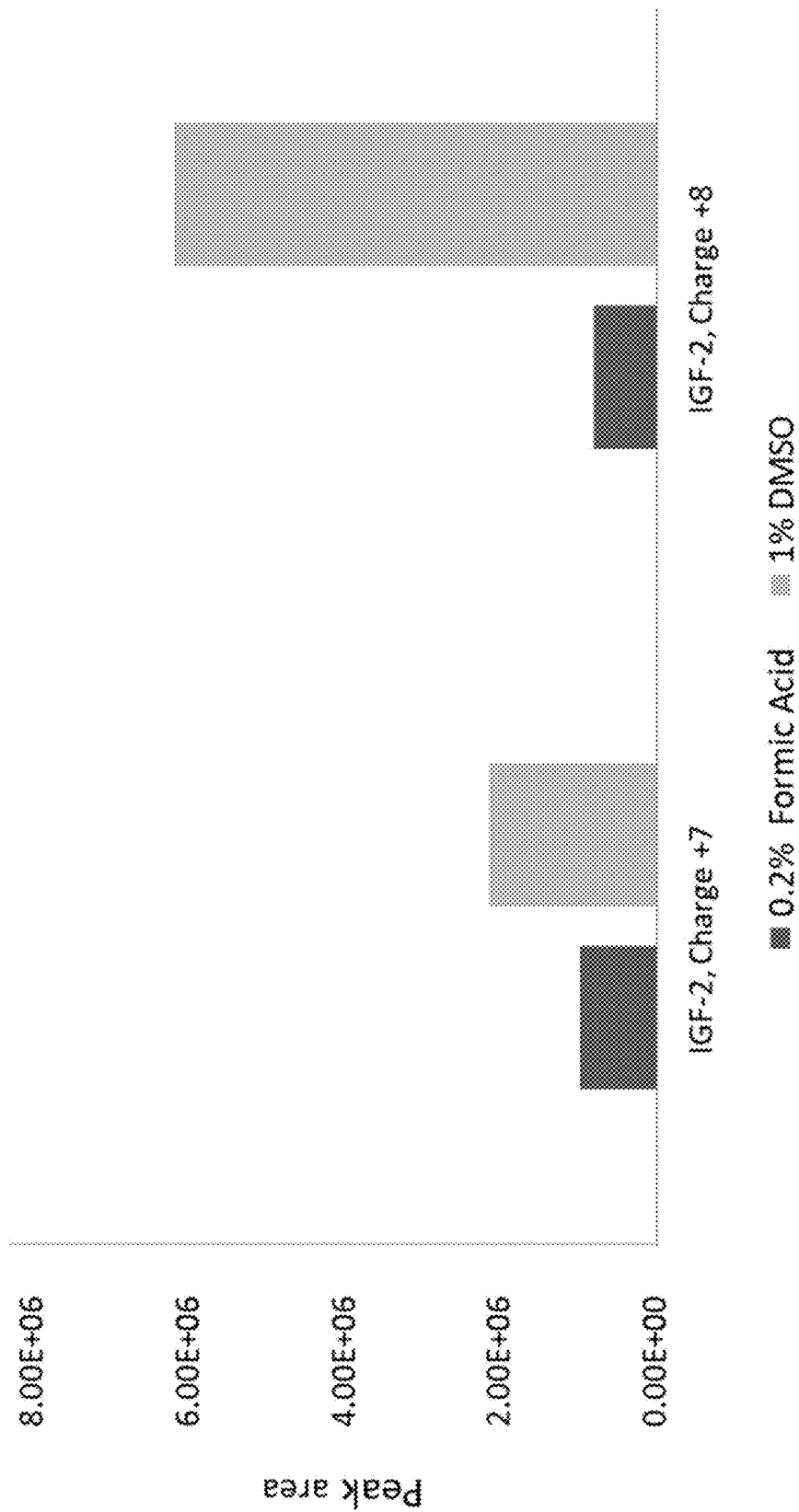
FIG. 7 shows a shift in the dominant charge state (from $7^+$ to $8^+$) in presence of DMSO for IGF-2 (B). IGF-2 charge state $7^+$, m/z 1067.9361 and charge state $8^+$, m/z 934.5699.

The increase in peak area observed when mobile phase additives are switched from 0.2% formic acid to 1% DMSO is shown for IGF-1 (FIG. 6) charge state $7^+$ (left side) and charge state $8^+$ (right side), and for IGF-2 (FIG. 7) charge state $7^+$ (left side) and charge state $8^+$ (right side). For both IGF-1 and IGF-2, inclusion of 1% DMSO in the mobile phase results in an increase in detectable signal (peak area) for both the $7^+$ and $8^+$ ions, but the observed increase was greater for the $8^+$ ion than for the $7^+$ ion.

Figure 8:
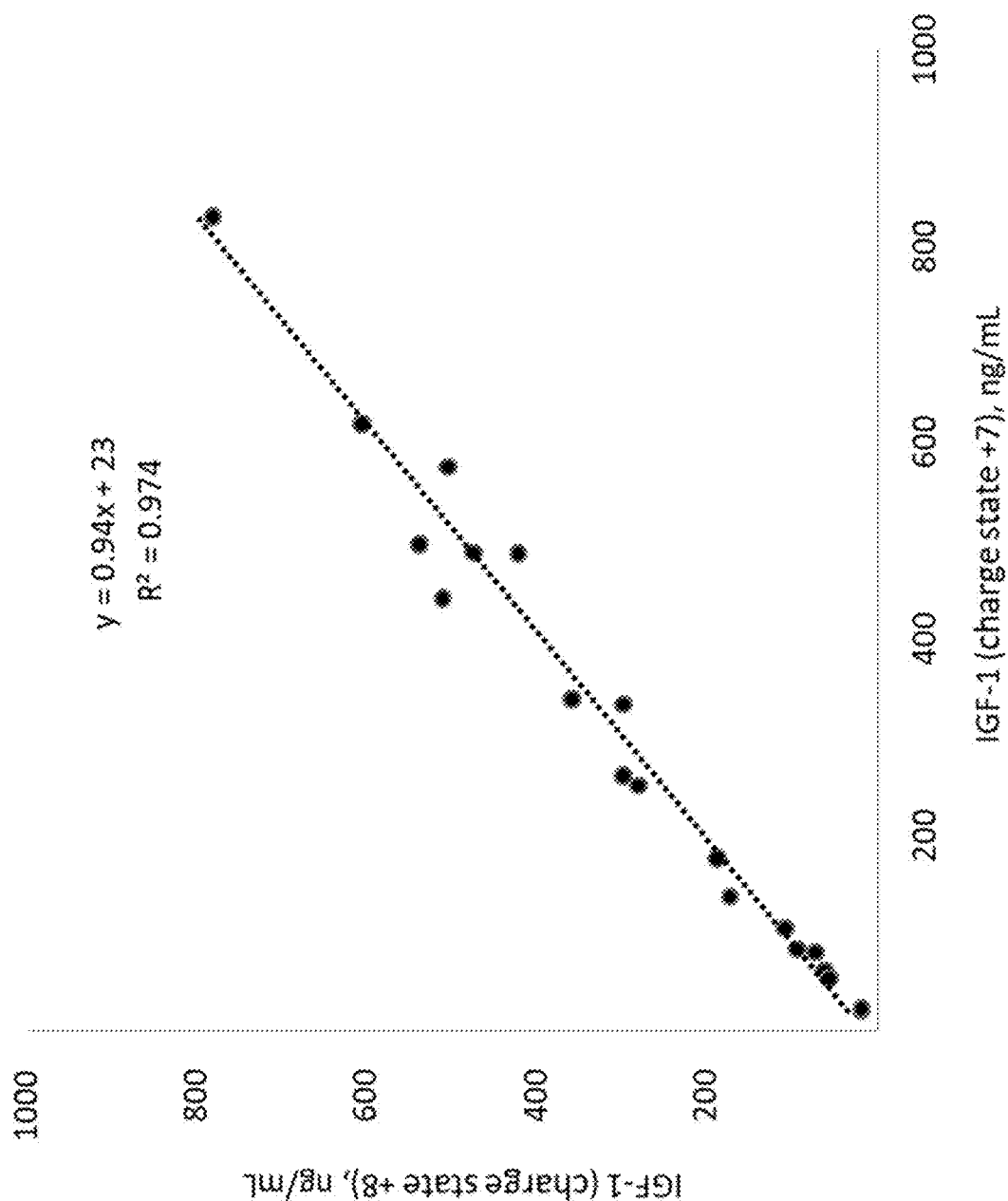
FIG. 8 shows a comparison of IGF-1 concentrations in patient serum samples quantified using ions of charge $7^+$ (m/z 1093.520) and charge $8^+$ (m/z 957.081).

To evaluate using the $8^+$ charge state for quantifying IGF-1 and compare the results obtained to those obtained when using the $7^+$ charge state, the IGF-1 concentrations in patient samples were quantified using ions of charge state $7^+$ (m/z 1093.520) and charge state $8^+$ (m/z 957.081), and the results were analyzed by linear regression (FIG. 8). The results obtained showed a strong correlation ($R^2$=0.974), demonstrating that quantification using the $8^+$ charge state ion was comparable to quantification using the $7^+$ charge state ion.

Example 3

Example Method's Performance
Sample Preparation

An example sample preparation is as follows: Sample preparation: (1) Prepare and print layout of the 96-well tube rack with sample IDs (8 wells per column, up to 12 columns). (2) Pull out specimens, controls and calibrators from the freezer and let equilibrate at room temperature (RT; 18-24° C.). (3) While samples thaw, label three 96 deep-well plates with the date and run number. (4) When the calibrators, controls and samples are defrosted, mix contents of the tubes by inverting racks with the tubes 15-20 times (5) Centrifuge tubes with calibrators and controls at 1,000×g for 1 min. (6) Prepare calibrators and aliquot in wells of the 96-well plate (plate #1). (7) Aliquot 100 μL of samples and controls into the corresponding wells of 96 well plate (plate #1). (8) Add to each sample and control 20 μL of $^{15}$N-labeled IGF-1 internal standard. (9) Secure silicon plate mat on top of plate and set the plate on orbital mixer (mix at 500 rpm for 30 min). (10) Remove plate mat and add to each well 400 UL of acidified ethanol (87.5% Ethanol 12.5% HCl). (11) Secure silicon plate mat and mix on plate mixer at 500 rpm for 15 mins at RT. (12) Centrifuge plate at 4° C. at 2,000×g for 20 mins. (13) Remove plate mat, transfer 300 μL of the supernatant to a new 96 well plate (plate #2). (14) Add to the wells 60 μL of cold 1.5 M Tris. (15) Secure silicon plate mat and set the plate on orbital mixer (mix at 500 rpm for 5 min). (16) Incubate the 96 well plate (plate #2) at −20° C. for 30 mins. (17) Centrifuge plate at 4° C. at 3,200×g for 10 mins. (18) Add 150 μL CLRW to a new 96 well plate. (19) Remove plate mat from the 96-well plate #2 and transfer 150 μL of the supernatant into the 96 well plate containing 150 μL CLRW (plate #3). (20) Seal plate with foil, set the plate on orbital mixer (mix at 500 rpm for 5 min). (21) Centrifuge plate at 4° ° C. at 3,200×g for 5 mins.

TABLE 5

Preparation of calibrators, QC, and patient samples.

| Sample | IGF-1, ng/mL | Sample volume, μL | IGF-1 concentration, ng/mL | IGF-1 Spiking Cal. Std. Volume added, μL | Mass spec gold serum matrix, Volume added, μL |
|---|---|---|---|---|---|
| Calibrator 1 | 10 | na | 500 ng/mL | 2 | 98 |
| Calibrator 2 | 50 | na | 500 ng/mL | 10 | 90 |
| Calibrator 3 | 100 | na | 500 ng/mL | 20 | 80 |
| Calibrator 4 | 300 | na | 6000 ng/mL | 5 | 95 |
| Calibrator 5 | 600 | na | 6000 ng/mL | 10 | 90 |
| Calibrator 6 | 1200 | na | 6000 ng/mL | 20 | 80 |
| Negative control | 0 | na | na | na | 100 |
| QC and patient samples | na | 100 | na | na | na |

HPLC Method

The HPLC method used for the analysis is as follows: prepared samples are analyzed using LC-MS method, utilizing chromatographic separation on multiplexing HPLC and high-resolution detection of intact IGF-1. HPLC column for $1^{st}$ dimensions separation: a) method 1 cartridge Chromolith RP-18 endcapped 5-2 (part #1520090001, Supelco), b) method 2: cartridge CN AJ0-4305 in SecurityGuard guard cartridge holder (KJ0-4282, both from Phenomenex). HPLC column for analytical separation ($2^{nd}$ dimension separation) Hypersil Gold C8, 2.1×50, 5 μm (part #25205-052130, Thermo Fisher). The $1^{st}$ and $2^{nd}$ dimension columns are connected to a valve interface module.

Mobile phase A1: 0.2% Formic Acid in water
Mobile phase B1: 0.2% Formic Acid in acetonitrile
Mobile phase C: 0.2% Formic Acid in 80% acetonitrile/ 19.8% isopropanol
Mobile phase A2: 5 mM acetic acid/1% DMSO/99% water
Mobile phase B2: 5 mM acetic acid/1% DMSO/99% acetonitrile
Autosampler wash solvent 1: 30%:30%:30%:10% of acetonitrile:isopropanol:methanol:water
Autosampler wash solvent 2: 0.1% formic acid in water.
Mobile phase gradients are listed in Table 6 and Table 7.

TABLE 6

Gradient program for $1^{st}$ dimension (quaternary pumps).

| Step | Time (min) | Length (min) | Flow (mL/min) | A (%) | B (%) | C (%) |
|---|---|---|---|---|---|---|
| 0 | 0 | 0.5 | 1 | 95 | 5 | 0 |
| 1 | 0.5 | 0.5 | 0.2 | 95 | 5 | 0 |
| 2 | 1 | 1 | 1 | 70 | 30 | 0 |
| 3 | 2 | 0.1 | 1 | 70 | 30 | 0 |
| 4 | 2.1 | 1.5 | 1 | 70 | 30 | 0 |
| 5 | 3.6 | 1 | 1.5 | 10 | 0 | 90 |
| 6 | 4.6 | 1 | 1.5 | 90 | 0 | 10 |
| 7 | 5.6 | 1 | 1.5 | 10 | 0 | 90 |
| 8 | 6.6 | 1.2 | 1 | 95 | 5 | 0 |

TABLE 7

Gradient program for 2$^{nd}$ dimension (binary pumps).

| Step | Time (min) | Length (min) | Flow (mL/min) | % A | % B |
|---|---|---|---|---|---|
| 0 | 0 | 0.5 | 0.6 | 95 | 5 |
| 1 | 0.5 | 0.5 | 0.4 | 95 | 5 |
| 2 | 1 | 1 | 0.6 | 95 | 5 |
| 3 | 2 | 0.1 | 0.6 | 75 | 25 |
| 4 | 2.1 | 1.5 | 0.6 | 55 | 45 |
| 5 | 3.6 | 1 | 0.6 | 50 | 50 |
| 6 | 4.6 | 1 | 0.6 | 90 | 10 |
| 7 | 5.6 | 1 | 0.6 | 50 | 50 |
| 8 | 6.6 | 1.2 | 0.6 | 95 | 5 |

MS Method

The MS method used for the analysis is as follows: mass Spectrometer Exploris 240 (Thermo Scientific) is used in full scan mode to monitor the 8$^+$ charge state m/z of IGF-1, internal standard, and A67T/A70T. The instrument data collection settings and source conditions are listed in Table 8.

TABLE 8

Mass Spectrometer Conditions in Thermo Xcalibur Instrument Setup.

| | |
|---|---|
| Application Mode | Peptide |
| Method Duration (min) | 3.6 |
| Infusion mode | Liquid Chromatography |
| Default Charge State | 8 |
| Internal Mass Calibration | RunStart EASY-IC ™ |
| Global Parameters | Ion Source Type: H-ESI |
| | Spray Voltage: Static |
| | Positive Ion (V): 2900 |
| | Negative Ion (V): 2000 |
| | Gas Mode: Static |
| | Sheath Gas: 30 |
| | Aux Gas: 10 |
| | Sweep Gas: 2 |
| | Ion Transfer Tube Temp (° C.) 325 |
| | Vaporizer Temp (° C.) 300 |
| Scan Parameters | Scan Range (m/z) 800-1300 |
| | Obitrap Resolution 120000 |
| | RF Lens (%) 120 |
| | AGC Target: Standard |
| | Maximum Injection Time Mode: Auto |
| | Microscans: 2 |
| | Data Type: Profile |
| | Polarity: Positive |

Data Analysis
IGF-1 WT Quantitation:

TABLE 9

Mass-to-charge ratios (m/z) used in the data analysis method (quantitation and qualitative confirmation of wild type IGF-1 and the A67T/A70T variant).

| Quantitation Mass (Da) | Confirming Mass (Da) | ID |
|---|---|---|
| 957.0811 | 957.2061 | IGF-1 |
| 968.6720 | 968.5464 | $^{15}$N labeled IGF-1 |

Analytical Precision

Analytical Precision of the measurements was evaluated by analyzing three serum samples containing low, medium and high concentrations of IGF-1 and IGF-2. Samples used in the experiments were pools of discard patient serum samples. The serum sample pools were aliquoted in tubes in the amount sufficient for one day of experiments and stored at −20° C. On the day of the experiment, one tube with serum pool corresponding to each evaluated concentration level was defrosted; the samples were prepared and analyzed on the day of the sample preparation. Results of the experiments on evaluation of precision for IGF-1 and IGF-2 can be seen in Table 10 and Table 11.

TABLE 10

| Name | Measured IGF-1 concentration (ng/mL) | Day 1 Average (ng/mL)/standard deviation/ CV, % | Measured IGF-1 concentration (ng/mL) | Day 2 Average (ng/mL)/standard deviation/ CV, % |
|---|---|---|---|---|
| Sample 1 | 12.7 | 12.8/1.86/14.5% | 16.2 | 15.9/2.52/15.9% |
| | 11.0 | | 15.3 | |
| | 11.3 | | 18.0 | |
| | 11.4 | | 20.4 | |
| | 10.8 | | 15.2 | |
| | 13.9 | | 16.1 | |
| | 16.5 | | 12.2 | |
| | 12.0 | | 11.9 | |
| | 14.4 | | 16.1 | |
| | 14.1 | | 17.2 | |
| Sample 2 | 131 | 130/9.45/7.3% | 124 | 134/8.22/6/2% |
| | 116 | | 131 | |
| | 127 | | 139 | |
| | 121 | | 133 | |
| | 133 | | 123 | |
| | 131 | | 139 | |
| | 122 | | 137 | |
| | 149 | | 126 | |
| | 139 | | 133 | |
| | 130 | | 150 | |
| Sample 3 | 484 | 551/37.0/6.7% | 607 | 576/37.6/6.5% |
| | 514 | | 614 | |
| | 513 | | 528 | |
| | 553 | | 576 | |
| | 579 | | 554 | |
| | 577 | | 604 | |

TABLE 10-continued

| Name | Measured IGF-1 concentration (ng/mL) | Day 1 Average (ng/mL)/standard deviation/ CV, % | Measured IGF-1 concentration (ng/mL) | Day 2 Average (ng/mL)/standard deviation/ CV, % |
|---|---|---|---|---|
| | 601 | | 504 | |
| | 581 | | 579 | |
| | 561 | | 615 | |
| | 546 | | 578 | |

TABLE 11

Data on evaluation of imprecision for IGF-2.

| Name | Measured IGF-2 concentration (ng/mL) | Day 1 Average (ng/mL)/ standard deviation/ CV, % |
|---|---|---|
| Sample 1 | 55.9 | 55.9/4.1/7.4% |
| | 56.2 | |
| | 56.5 | |
| | 49.3 | |
| | 54.7 | |
| | 51.2 | |
| | 61.6 | |
| | 55.6 | |
| | 62.0 | |
| Sample 2 | 208 | 222.4/19.3/8.7% |
| | 228 | |
| | 247 | |
| | 183 | |
| | 235 | |
| | 238 | |
| | 235 | |
| | 211 | |
| | 231 | |
| | 208 | |
| Sample 3 | 637 | 640.4/49.8/7.8% |
| | 652 | |
| | 593 | |
| | 596 | |
| | 623 | |
| | 742 | |
| | 589 | |
| | 687 | |
| | 645 | |

Analytical Accuracy

Analytical accuracy was evaluated using add-mixing human serum samples containing IGF-1 concentration <50 ng/ml with a pool of patient samples containing elevated IGF-1 concentration at 5 different ratios (Table 12). The target IGF-1 concentrations are listed in Table 13 below and the accuracy was calculated by comparison of the measured concentration with the expected (IGF-1 present in the neat samples plus the amount added).

TABLE 12

Volumes of neat patient serum samples and the samples pool used in the add-mixing experiment.

| Level | Patient Sample (µL) | Patient sample containing 720 ng/ml of IGF-1 (µL) | Total Volume (µL) |
|---|---|---|---|
| 1 | 95 | 5 | 100 |
| 2 | 90 | 10 | 100 |
| 3 | 80 | 20 | 100 |
| 4 | 50 | 50 | 100 |
| 5 | 10 | 90 | 100 |

TABLE 13

Observed and measured concentrations of IGF-1 in samples analyzed for evaluation of the method accuracy.

| Levels | IGF-1 in neat sample (ng/ml) | IGF-1 in spiked sample (ng/mL) | Difference (ng/ml) | IGF-1 Added (ng/ml) | Accuracy | Avg. Accuracy |
|---|---|---|---|---|---|---|
| 1 | 32.0 | 66.8 | 34.8 | 36 | 97% | 88% |
| | 48.7 | 77.8 | 29.2 | | 81% | |
| | 34.0 | 66.0 | 32.0 | | 89% | |
| | 39.1 | 70.1 | 31.0 | | 86% | |
| 2 | 36.3 | 102 | 65.2 | 72 | 91% | 90% |
| | 37.1 | 109 | 72.3 | | 101% | |
| | 42.8 | 113 | 69.8 | | 97% | |
| | 45.8 | 98.2 | 52.4 | | 73% | |
| 3 | 45.1 | 164 | 119 | 144 | 83% | 92% |
| | 47.4 | 199 | 152 | | 105% | |
| | 43.5 | 161 | 118 | | 82% | |
| | 38.9 | 178 | 139 | | 96% | |
| 4 | 47.7 | 381 | 334 | 360 | 93% | 96% |
| | 39.7 | 371 | 332 | | 92% | |
| | 43.9 | 386 | 343 | | 95% | |
| | 39.9 | 414 | 374 | | 104% | |
| 5 | 32.2 | 662 | 630 | 647 | 97% | 95% |
| | 55.9 | 657 | 601 | | 93% | |
| | 46.3 | 632 | 585 | | 90% | |
| | 61.3 | 707 | 646 | | 100% | |

Comparison with LC-MS Method of a Commercial Laboratory

Figure 9:
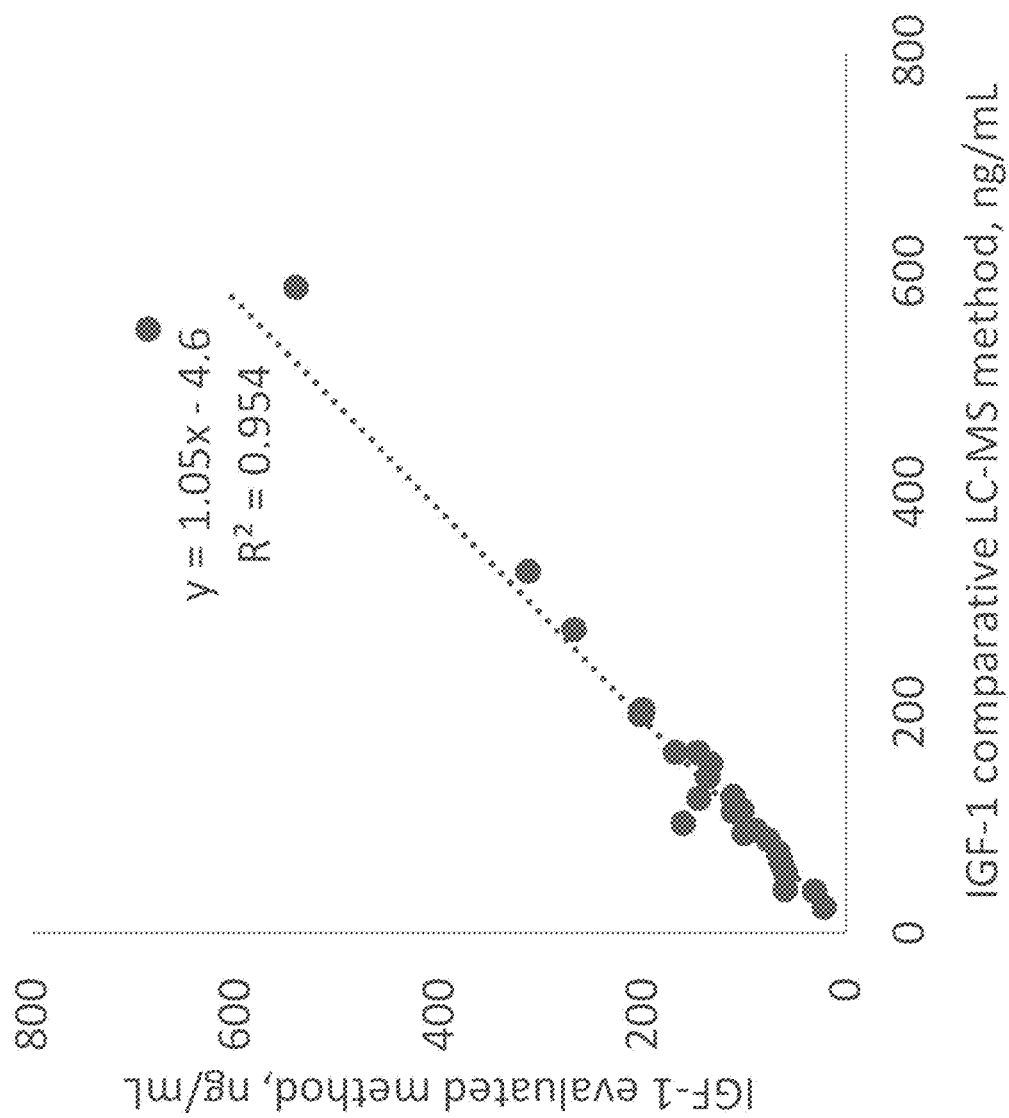
FIG. 9 a shows comparison of IGF-1 concentrations measured in neat patient samples analyzed by an example method and a comparative LC-MS method.

The method was compared to the LC-MS method of a commercial laboratory using a set of deidentified patient serum samples. FIG. 9 shows results of the method comparison.

Analytical Measurement Range

Analytical measurement range of the method was evaluated by replicate analysis of samples prepared by mixing serum pool containing low concentration of IGF-1 (~10 ng/mL) and a serum pool containing high IGF-1 concentration (~800 ng/ml). Table 14 below shows proportion in which the samples were mixed. The samples were analyzed in three replicates on two days. Table 15 below summarizes data of the evaluation of the assay linearity. The observed IGF-1 concentrations were within 15% of the expected concentration, and imprecision at all evaluated concentrations was <15% (Table 16).

TABLE 14

Volumes of the low and high pools of patient serum samples used for preparing samples for the experiment on evaluation of the analytical measurement range of the method.

| Level | Volume Low patient pool (µL) | Volume High patient pool (µL) | Total Volume (µL) |
|---|---|---|---|
| 1 | 100 | 0 | 100 |
| 2 | 90 | 10 | 100 |
| 3 | 75 | 25 | 100 |

TABLE 14-continued

Volumes of the low and high pools of patient serum samples used for preparing samples for the experiment on evaluation of the analytical measurement range of the method.

| Level | Volume Low patient pool (µL) | Volume High patient pool (µL) | Total Volume (µL) |
|---|---|---|---|
| 4 | 60 | 40 | 100 |
| 5 | 50 | 50 | 100 |
| 6 | 40 | 60 | 100 |
| 7 | 25 | 75 | 100 |
| 8 | 10 | 90 | 100 |
| 9 | 0 | 100 | 100 |

TABLE 15

Summary of the results of evaluation of the analytical measurement range of the method.

| Sample | Day 1 Expected | Day 1 Conc. (ng/ml) | Day 1 Avg. (ng/ml) | Day 1 Accuracy | Day 1 Avg. Accuracy | CV |
|---|---|---|---|---|---|---|
| AMR 1 | 10 | 10.4 | 10.6 | 104% | 106% | 2% |
|  |  | 10.8 |  | 108% |  |  |
| AMR 2 | 83 | 71 | 78.5 | 86% | 95% | 7% |
|  |  | 83 |  | 100% |  |  |
|  |  | 82 |  | 99% |  |  |
| AMR 3 | 191 | 188 | 201.7 | 98% | 106% | 6% |
|  |  | 217 |  | 114% |  |  |
|  |  | 200 |  | 105% |  |  |
| AMR 4 | 299 | 305 | 315.5 | 102% | 106% | 3% |
|  |  | 314 |  | 105% |  |  |
|  |  | 328 |  | 110% |  |  |
| AMR 5 | 371 | 457 | 414.0 | 123% | 112% | 8% |
|  |  | 380 |  | 102% |  |  |
|  |  | 405 |  | 109% |  |  |
| AMR 6 | 443 | 470 | 477.0 | 106% | 108% | 1% |
|  |  | 479 |  | 108% |  |  |
|  |  | 482 |  | 109% |  |  |
| AMR 7 | 551 | 619 | 579.8 | 112% | 105% | 5% |
|  |  | 551 |  | 100% |  |  |
|  |  | 570 |  | 103% |  |  |
| AMR 8 | 659 | 697 | 684.6 | 106% | 104% | 1% |
|  |  | 681 |  | 103% |  |  |
|  |  | 676 |  | 103% |  |  |
| AMR 9 | 700 | 718 | 730.9 | 103% | 104% | 2% |
|  |  | 744 |  | 106% |  |  |

Evaluation of the method's sensitivity was performed by analysis of samples containing progressively lower concentration of IGF-1. The samples were prepared as follows, a sample containing 60 ng/ml of IGF-1 was diluted with MS Gold serum (MSGS, item MSG3000, Golden West Diagnostics) in proportions listed in Table 16; results of the analysis of these samples are shown in Table 16.

TABLE 16

Samples for evaluation of the method's sensitivity.

| Sample | IGF-1 (ng/mL) | Avg Conc. (ng/mL) | Accuracy, % | Imprecision, % |
|---|---|---|---|---|
| Sample | 53.8 | 59.1 | 107% | 9% |
|  | 64.5 |  |  |  |
| Sample diluted with MSGS 9:1 | 48.3 52.2 | 50.2 | 94% | 4% |
| Sample diluted with MSGS 1:1 | 31.1 25.5 | 28.3 | 96% | 10% |
| Sample diluted with MSGS 1:9 | 6.2 4.8 | 5.5 | 93% | 13% |

Figure 10:
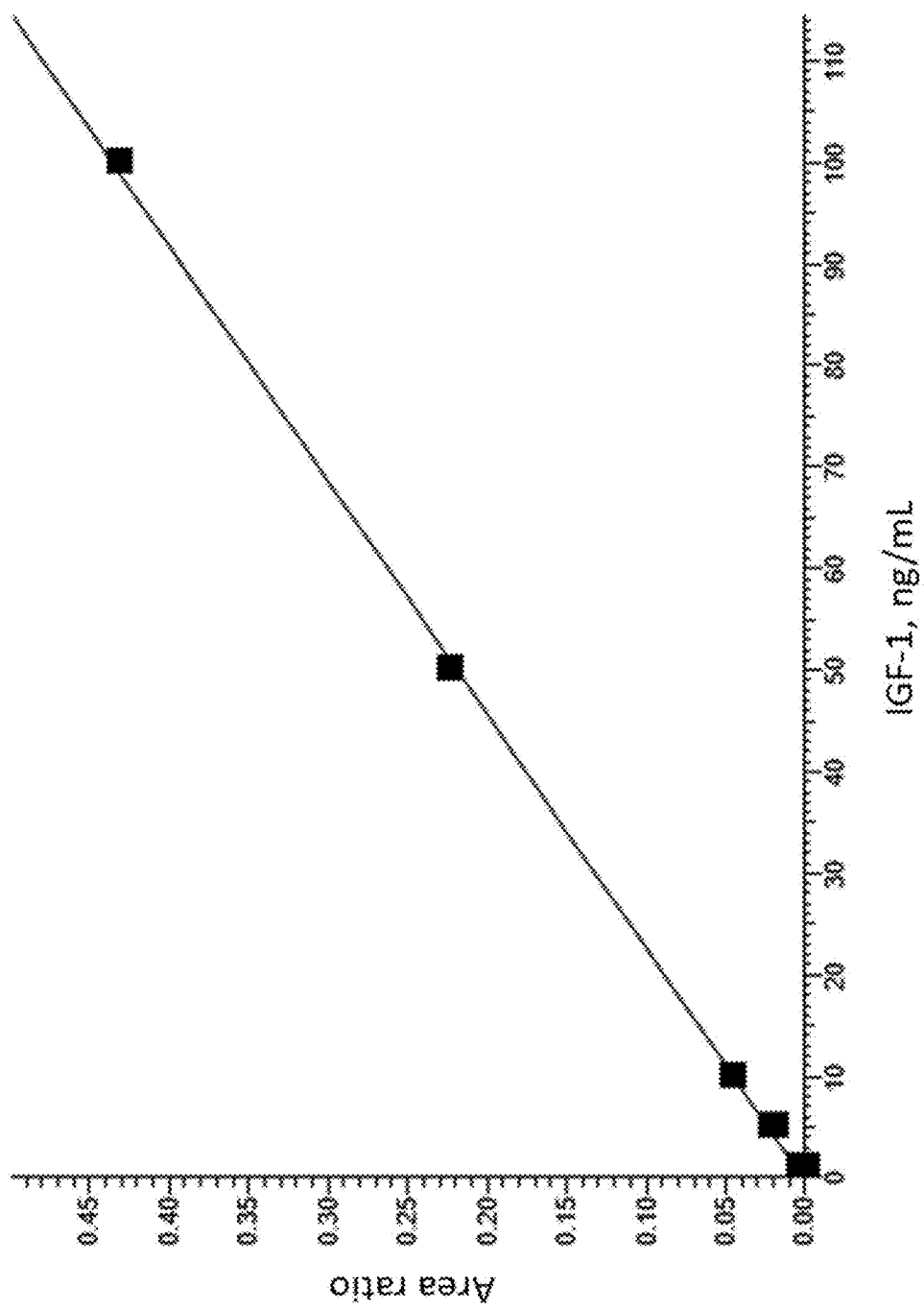
FIG. 10 shows a calibration curve (IGF-1 quantified using ion m/z 957.081, charge $8^+$).
Figure 11:
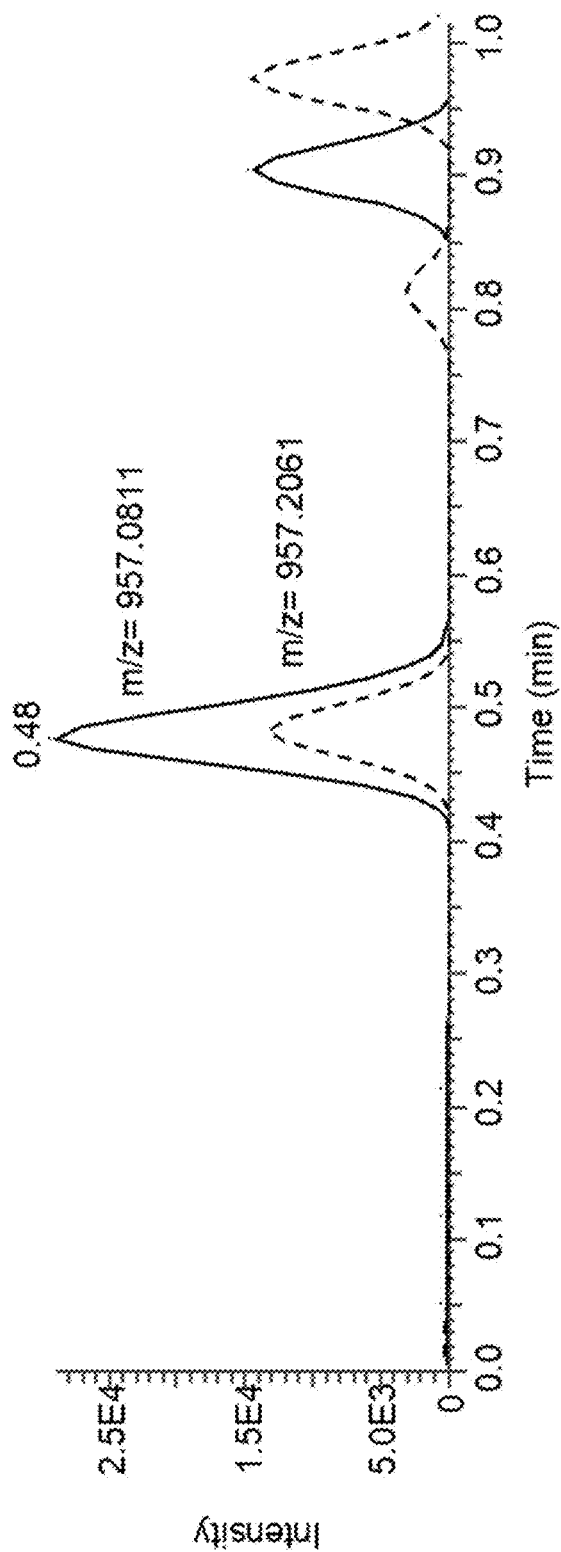
FIG. 11 shows a chromatographic peak of IGF-1 in a sample containing 1 ng/ml of IGF-1 (quantified using ion m/z 957.0811, qualitative confirmation using ion m/z 957.2061, both ions charge $8^+$).

Experiments on evaluation of the limit of detection (LOD) and limit of quantitation (LLOQ) were performed as follows. Calibration standards were prepared at concentration 1, 5, 10, 50 and 100 ng/ml (FIG. 10). Serum sample containing 20 ng/ml of IGF-1 was prepared by pooling residual deidentified patient serum samples containing 10-30 ng/ml of IGF-1; samples with lower IGF-1 concentration were prepared by progressive dilution of the sample pool using MSGS as the diluent. IGF-1 concentrations targeted in the samples were 20, 10, 5, 2.5, 1.25 and 0.63 ng/ml. The samples were analyzed in duplicate over two days. Mean values of imprecision (accuracy) and the evaluated concentrations were 17% (106%), 7% (99%), 5% (97%), 12% (106%) and 28% (87%). The disclosed method was tested at low concentrations of IGF-1 as follows: samples containing 1 ng/ml of IGF-1 were analyzed and the chromatographic peak corresponding to IGF-1 was quantified using $8^+$ ion m/z 957.0811 and qualitatively confirmed using $8^+$ ion m/z 957.206. A representative chromatogram showing the co-elution of the m/z 957.0811 ion (solid line) and m/z 957.2061 ion (dotted line) is provided at FIG. 11.

Method imprecision for IGF-1 in samples containing <50 ng/ml of IGF-1 was evaluated by analysis of neat residual patient samples; results of analysis are summarized in Table 17.

TABLE 17

Evaluation of IGF-1 method performance using neat residual patient samples containing <50 ng/mL of IGF-1.

| Sample | Calc. Conc. (ng/mL) | IGF-1 (ng/mL) | % CV |
|---|---|---|---|
| Sample-01 | 39.2 40.3 | 39.8 | 1.3% |
| Sample-02 | 37.4 33.2 | 35.3 | 6.0% |
| Sample-03 | 41.9 44.4 | 43.1 | 2.9% |
| Sample-04 | 37.0 34.3 | 35.7 | 3.8% |
| Sample-05 | 40.7 43.9 | 42.3 | 3.9% |
| Sample-06 | 54.4 54.9 | 54.7 | 0.5% |
| Sample-07 | 38.0 44.3 | 41.2 | 7.7% |
| Sample-08 | 53.9 48.8 | 51.4 | 4.9% |
| Sample-09 | 52.2 50.2 | 51.2 | 2.0% |
| Sample-10 | 38.4 40.2 | 39.3 | 2.3% |
| Sample-11 | 38.8 34.8 | 36.8 | 5.4% |

Assessment of carryover was performed by analysis of pool of neat serum samples containing low IGF-1 concentration (15 ng/ml) and high IGF-1 (3,200 ng/ml) concentration in a sequence L1, L2, L3, H1, H2, L4, H3, H4, L5, L6, L7, L8, H5, H6, L9, H7, H8, L10, H9, H10, L11. The samples were prepared, analyzed on the instrument and the results were assessed using EP evaluator software. The observed level of carryover passed the acceptance criteria.

It is understood that the foregoing detailed description and accompanying examples are merely illustrative and are not to be taken as limitations upon the scope of the invention.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method of determining a concentration of insulin-like growth factor-1 (IGF-1) in a sample, the method comprising:
   a) subjecting the sample to high performance liquid chromatography (HPLC) utilizing a mobile phase comprising DMSO at about 1% by volume of the mobile phase;
   b) ionizing the sample to produce one or more ions detectable by mass spectrometry, thereby producing an amount of IGF-1 ions in an $8^+$ charge state that is greater than an amount of IGF-1 ions in a $6^+$ charge state or an amount of IGF-1 ions in a $7^+$ charge state;
   c) determining an amount of IGF-1 ions in an $8^+$ charge state by mass spectrometry; and
   d) relating the amount of the determined IGF-1 ions in the $8^+$ charge state to the concentration of IGF-1 in the sample,
   wherein the method has a limit of detection (LOD) of less than or equal to 4 ng/ml.

2. The method of claim 1, wherein determining the amount of IGF-1 ions in the $8^+$ charge state comprises determining the amount of an ion having a mass-to-charge ratio of 957.1±1 Da.

3. The method of claim 1, wherein the HPLC utilizes a primarily aqueous-based mobile phase and a primarily organic-based mobile phase, and wherein the primarily aqueous-based mobile phase, the primarily organic-based mobile phase, or both include DMSO.

4. The method of claim 3, wherein the primarily aqueous-based mobile phase, the primarily organic-based mobile phase, or a combination thereof further includes an organic acid.

5. The method of claim 3, wherein the primarily organic-based mobile phase further includes an organic acid and acetonitrile.

6. The method of claim 5, wherein the organic acid comprises acetic acid, formic acid, difluoroacetic acid, or a combination thereof.

7. The method of claim 3, wherein the primarily aqueous-based mobile phase includes, by percent volume of the primarily aqueous-based mobile phase:
   about 0.02% to about 0.3% acetic acid, wherein the remaining balance is water.

8. The method of claim 3, wherein the primarily organic-based mobile phase includes, by percent volume of the primarily organic-based mobile phase:
   about 0.02% to about 0.3% acetic acid; wherein the remaining balance is acetonitrile.

9. The method of claim 1, further comprising purifying the sample via in-line solid phase extraction (SPE) prior to subjecting the sample to HPLC.

10. The method of claim 1, wherein the sample comprises plasma or serum.

11. The method of claim 1, further comprising adding an internal standard to the sample and detecting an amount of the internal standard.

12. The method of claim 1, wherein the mass spectrometry is performed with a high-resolution mass spectrometry instrument having a mass resolution of ≥30,000 and a mass accuracy of ≤15 ppm.

13. The method of claim 1, wherein the ionizing is performed by electrospray ionization (ESI).

14. The method of claim 1, wherein the HPLC utilizes a reverse phase column or an ion-exchange column.

15. The method of claim 1, wherein the method has a lower limit of quantification (LLOQ) of less than or equal to 12 ng/mL.

16. A method of determining a concentration of insulin-like growth factor-1 (IGF-1) in a sample, the method comprising:
   a) subjecting the sample to high performance liquid chromatography (HPLC) utilizing a mobile phase comprising DMSO at about 1% by volume of the mobile phase and an organic acid;
   b) ionizing the sample to produce one or more ions detectable by mass spectrometry, thereby producing an amount of IGF-1 ions in an $8^+$ charge state that is greater than an amount of IGF-1 ions in a $6^+$ charge state or an amount of IGF-1 ions in a $7^+$ charge state;
   c) determining the amount of IGF-1 ions in the $8^+$ charge state by mass spectrometry; and
   d) relating the amount of the determined IGF-1 ions in the $8^+$ charge state to the concentration of IGF-1 in the sample.

17. The method of claim 16, wherein the mobile phase comprises the organic acid at about 0.05% to about 0.3% by volume of the mobile phase.

18. The method of claim 16, wherein the organic acid is acetic acid.

19. The method of claim 18, wherein the HPLC utilizes:
   a primarily aqueous-based mobile phase including, by percent volume of the primarily aqueous-based mobile phase, about 1% DMSO and about 0.05% to about 0.3% acetic acid, wherein the remaining balance is water, and
   a primarily organic-based mobile phase including, by percent volume of the primarily organic-based mobile phase, about 1% DMSO and about 0.05% to about 0.3% acetic acid, wherein the remaining balance is acetonitrile.

* * * * *